United States Patent [19]

Oddsen et al.

[11] Patent Number: 5,220,928
[45] Date of Patent: Jun. 22, 1993

[54] SURGICAL PROCEDURE FOR JOINING TISSUE IN AN INTERNAL BODY CAVITY

[75] Inventors: Robert R. Oddsen, Centerport; Ralph Ger, Lake Success, both of N.Y.

[73] Assignee: Stryker Sales Corporation, Kalamazoo, Mich.

[21] Appl. No.: 830,216

[22] Filed: Jan. 31, 1992

Related U.S. Application Data

[60] Division of Ser. No. 493,046, Mar. 12, 1990, Pat. No. 5,125,553, which is a continuation-in-part of Ser. No. 341,155, Apr. 20, 1989, abandoned, and a continuation-in-part of Ser. No. 185,054, Apr. 22, 1988, Pat. No. 4,944,443, and a continuation-in-part of Ser. No. 195,586, May 18, 1988, Pat. No. 4,919,152, said Ser. No. 341,155, is a continuation-in-part of Ser. No. 185,054, said Ser. No. 195,586, is a continuation of Ser. No. 20,555, Mar. 2, 1987, abandoned, which is a continuation of Ser. No. 815,659, Dec. 30, 1985, abandoned, which is a continuation of Ser. No. 525,125, Aug. 22, 1983, abandoned.

[51] Int. Cl.$^5$ ............................................. A61B 17/04
[52] U.S. Cl. .................................... 128/898; 227/175; 227/178
[58] Field of Search ........................ 606/219; 128/898; 227/19, 20, 175, 176, 177, 178, 181

[56] References Cited

U.S. PATENT DOCUMENTS

| | | |
|---|---|---|
| 641,036 | 1/1900 | Pilling . |
| 2,011,169 | 8/1935 | Wappler . |
| 2,034,785 | 3/1936 | Wappler . |
| 2,384,697 | 9/1945 | Riccardi . |
| 3,275,211 | 9/1966 | Hirsch et al. ............... 227/19 |
| 3,585,985 | 6/1971 | Gould . |
| 3,592,377 | 7/1971 | Green . |
| 3,882,854 | 5/1975 | Hulka et al. . |
| 4,038,987 | 8/1977 | Komiya . |
| 4,049,002 | 9/1977 | Kletschka et al. . |
| 4,101,063 | 7/1978 | Kapitanov et al. ........... 227/19 |
| 4,111,206 | 9/1978 | Vishnevsky et al. ......... 227/19 X |
| 4,122,856 | 10/1978 | Mosior et al. . |
| 4,235,238 | 11/1980 | Ogiu et al. . |
| 4,257,419 | 3/1981 | Goltner et al. . |
| 4,273,129 | 6/1981 | Boebel . |
| 4,424,810 | 1/1984 | Jewusiak . |
| 4,485,953 | 12/1984 | Rothfuss . |
| 4,505,414 | 3/1985 | Filipi ...................... 227/155 X |
| 4,595,007 | 6/1986 | Mericle . |
| 4,784,137 | 11/1988 | Kulik et al. . |

FOREIGN PATENT DOCUMENTS

| | | |
|---|---|---|
| 293929 | 9/1916 | Fed. Rep. of Germany . |
| 2417621 | 11/1974 | Fed. Rep. of Germany . |
| 2330182 | 1/1975 | Fed. Rep. of Germany . |
| 2553540 | 6/1977 | Fed. Rep. of Germany . |
| 8300615 | 3/1983 | PCT Int'l Appl. . |
| 8505025 | 11/1985 | PCT Int'l Appl. . |

OTHER PUBLICATIONS

Ger, Ralph "The Management of Certain Abdominal Herniae By Intra-Abdominal Closure of the Neck of the Sac", Annals of the Royal College of Surgeons of England, pp. 342-344, Sep. 1982.

*Primary Examiner*—Stephen C. Pellegrino
*Assistant Examiner*—Jeffrey A. Schmidt
*Attorney, Agent, or Firm*—Rosen, Dainow & Jacobs

[57] ABSTRACT

A surgical procedure is disclosed for joining, e.g., by stapling or clipping, body tissue of a patient situated in an internal body cavity of the patient from within the body cavity through a small opening into the body cavity. For example, the surgical procedure may be employed to repair indirect inquinial or femoral hernias in a laparoscopic procedure. A small opening is made into the body cavity at a site on the patient's body remote from the body tissue to be joined in the internal body cavity. The body cavity is insufflated. An elongate tissue-joining instrument is inserted into the body cavity through the small opening. The instrument is moved through the insufflated internal body cavity to position a distal end of the instrument close to and on an internal side of the body tissue to be joined in the body cavity. The pieces of body tissue are then joined by the instrument by manipulation of the instrument at a proximal end thereof.

23 Claims, 15 Drawing Sheets

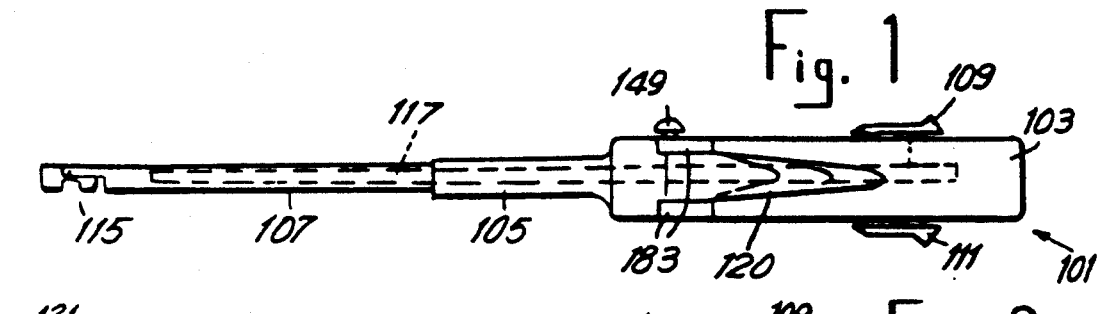
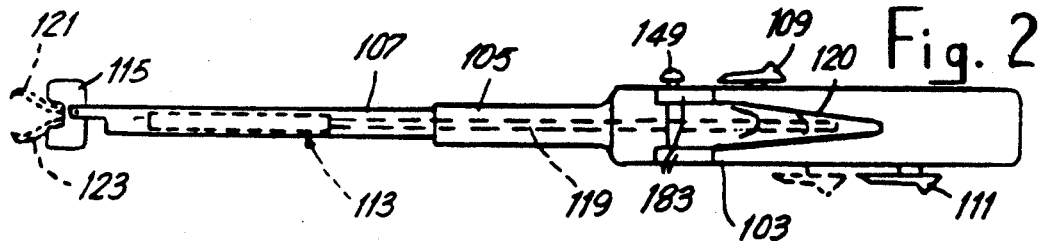
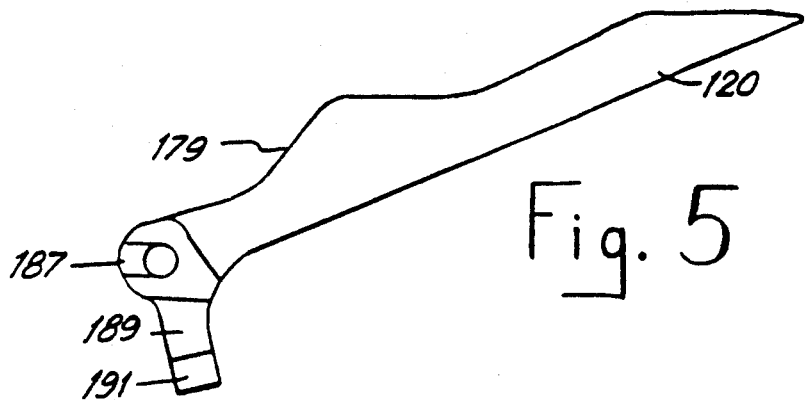
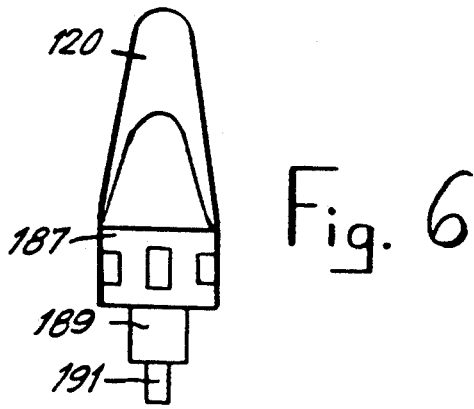

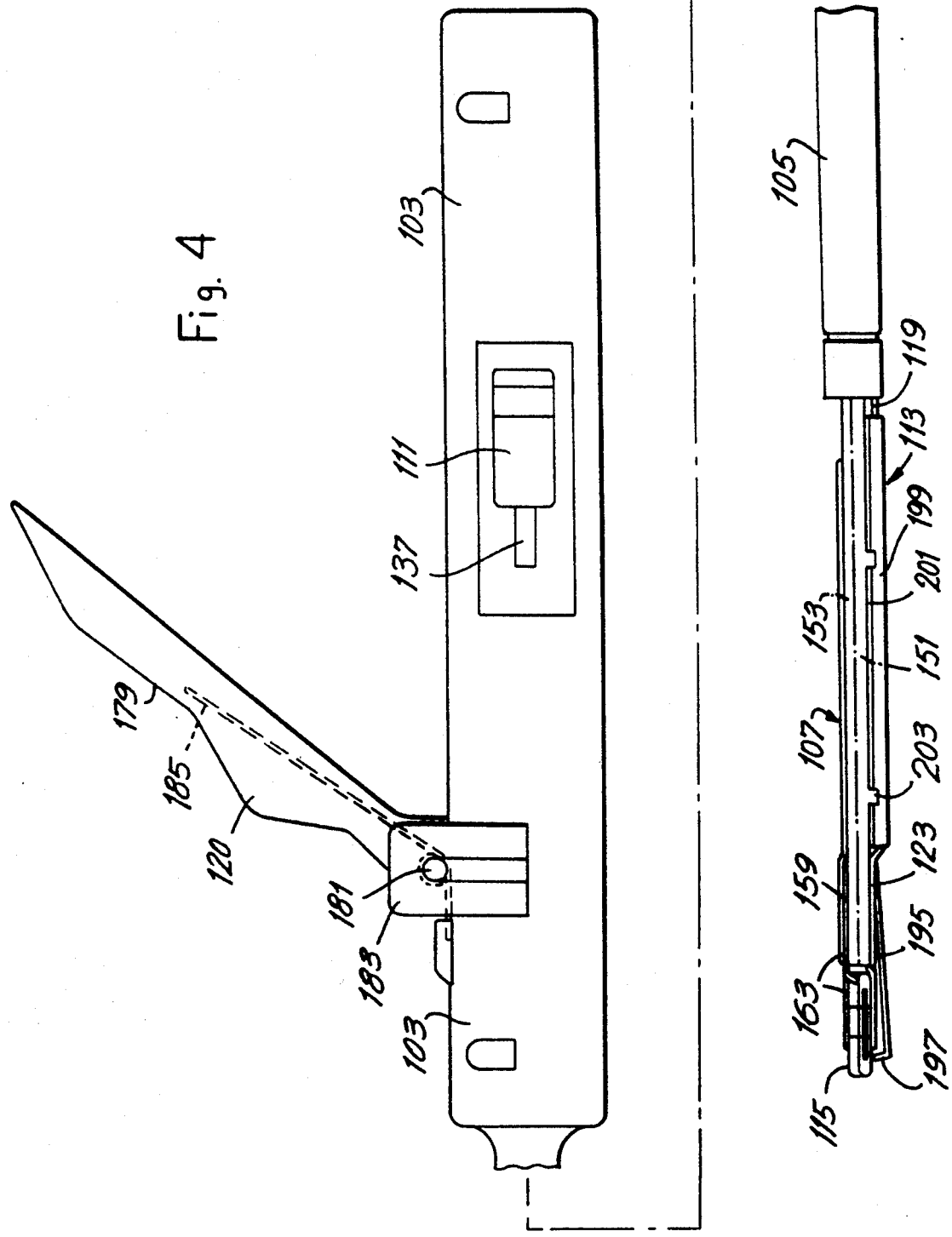

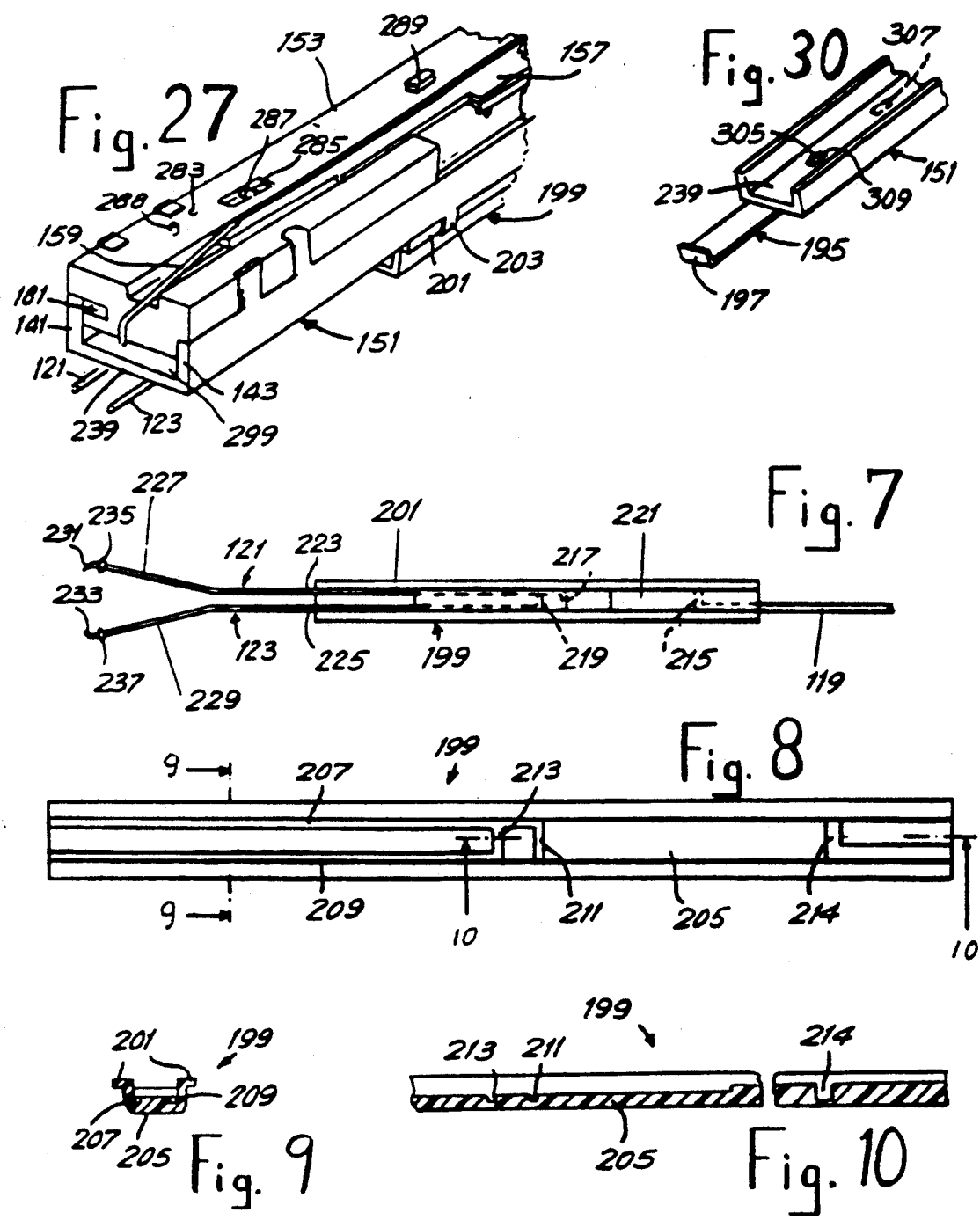

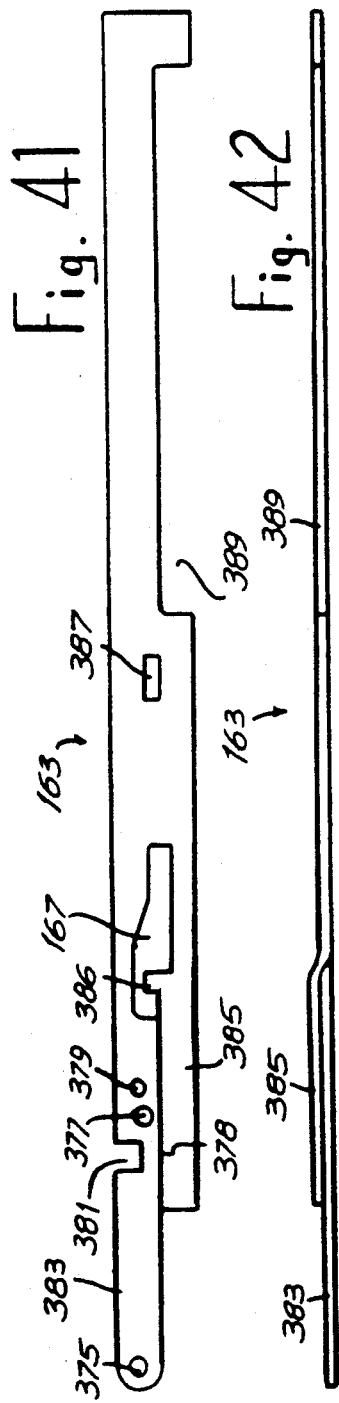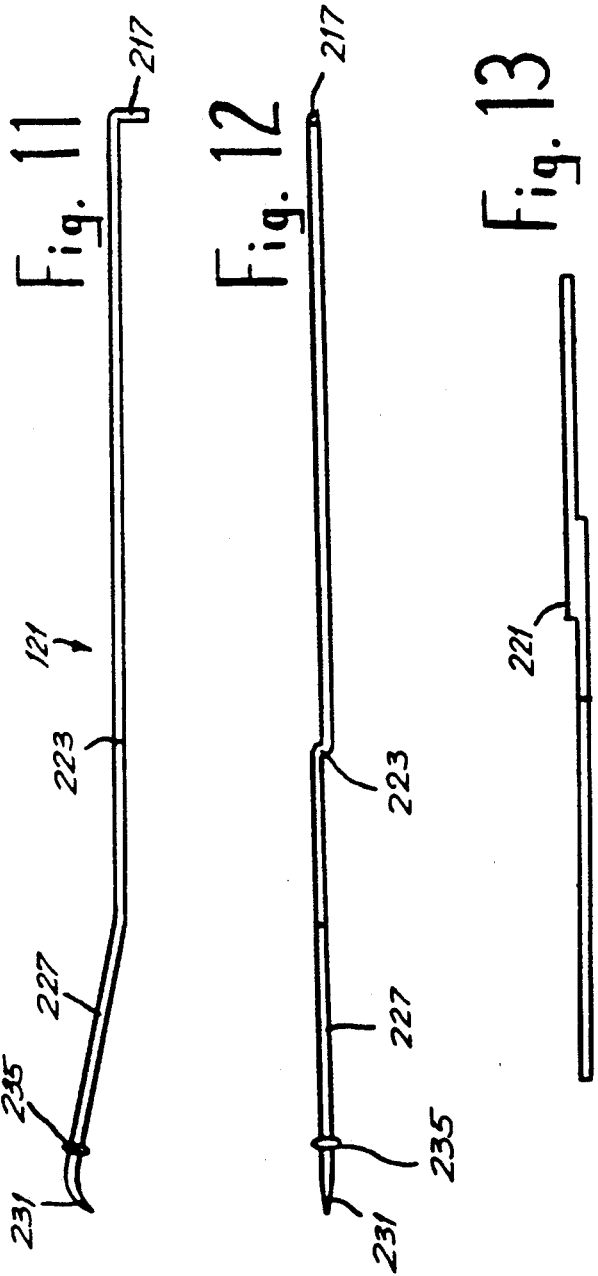

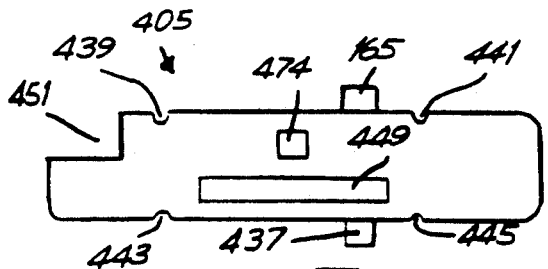
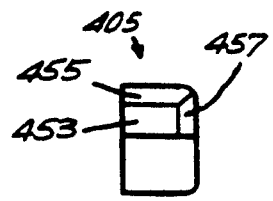

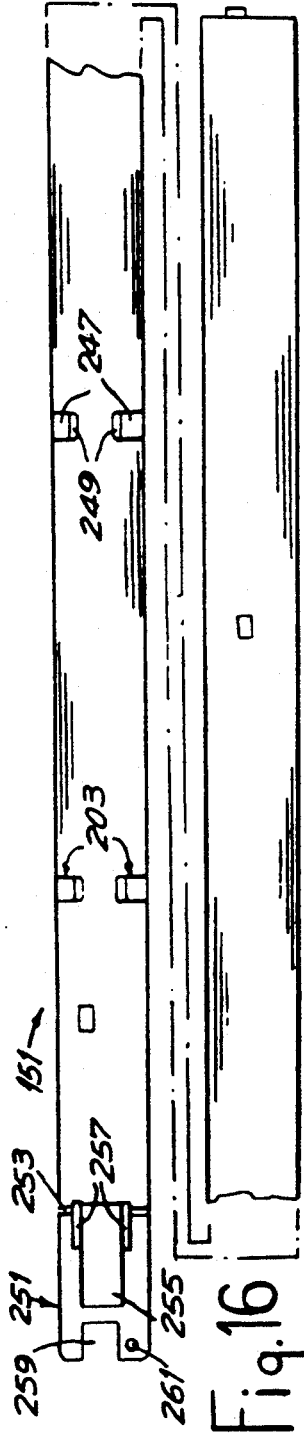
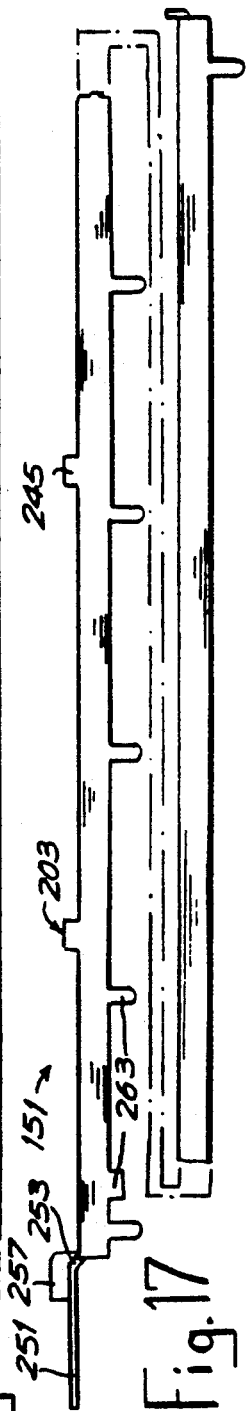
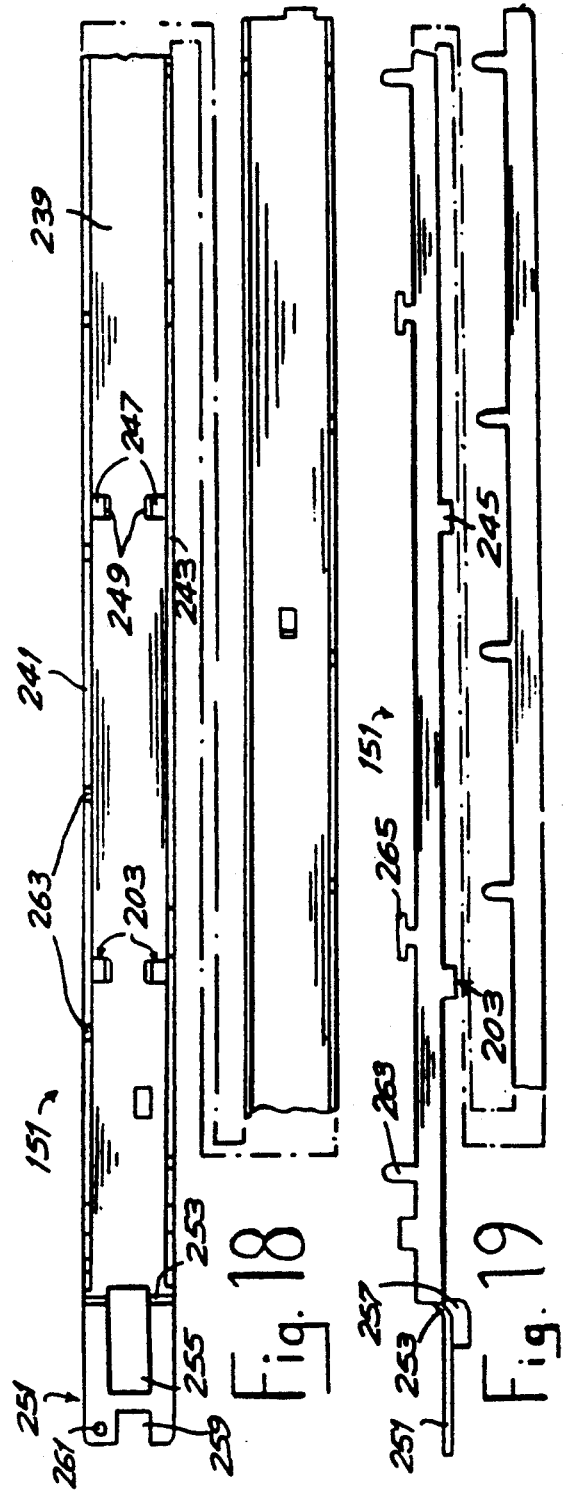
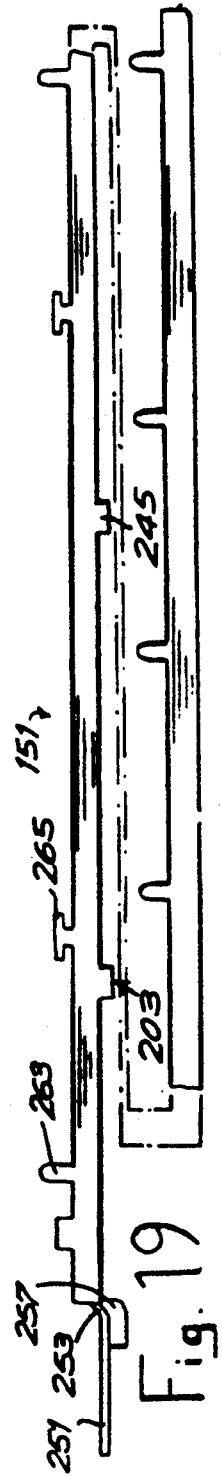

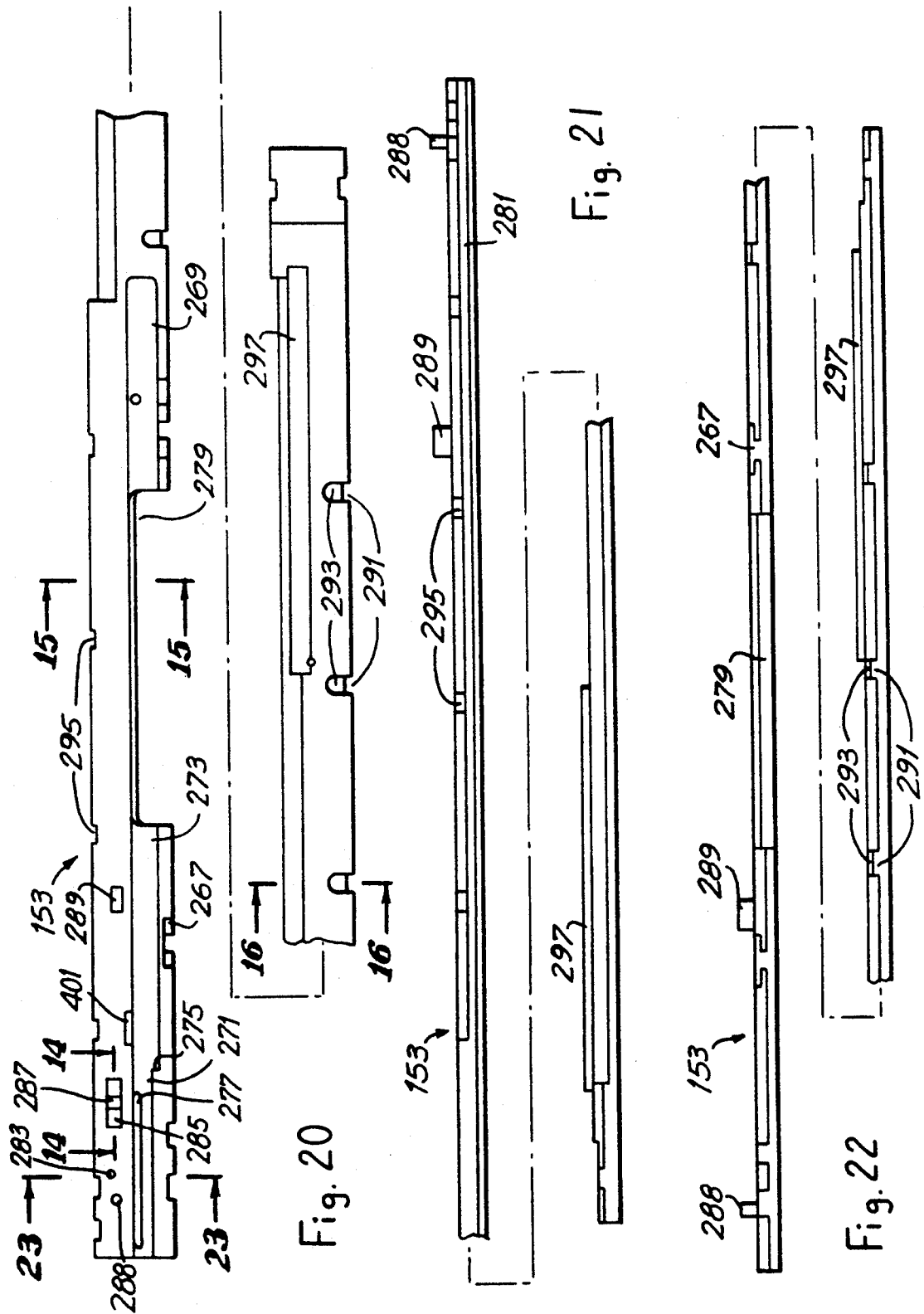

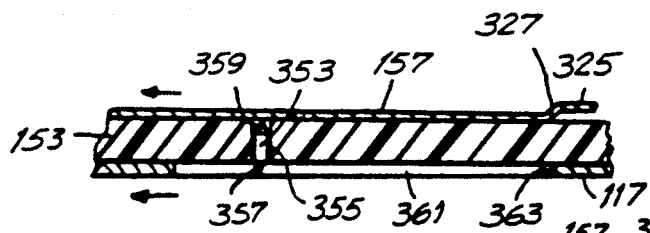
Fig. 38
Fig. 39
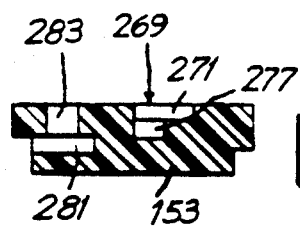
Fig. 23
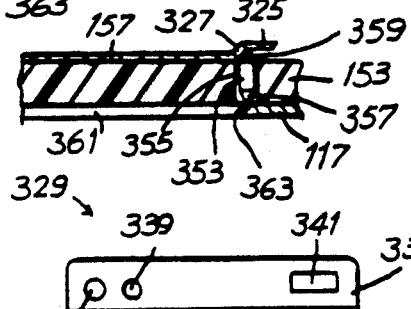
Fig. 33
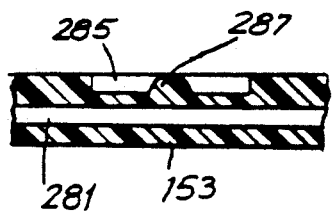
Fig. 24
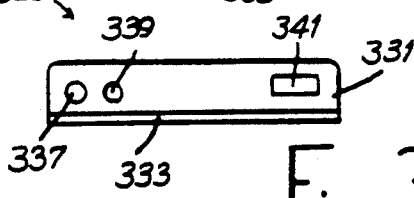
Fig. 34
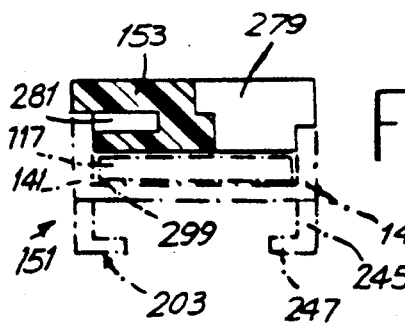
Fig. 25
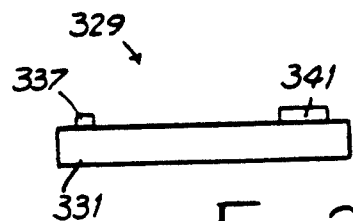
Fig. 35
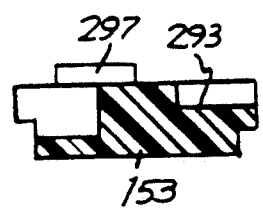
Fig. 26
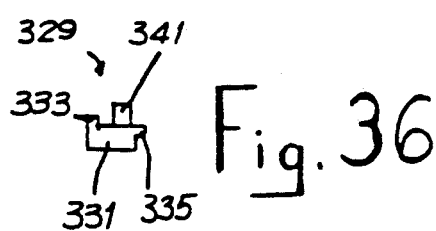
Fig. 36

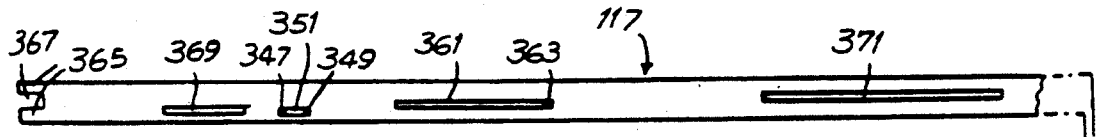
Fig. 40
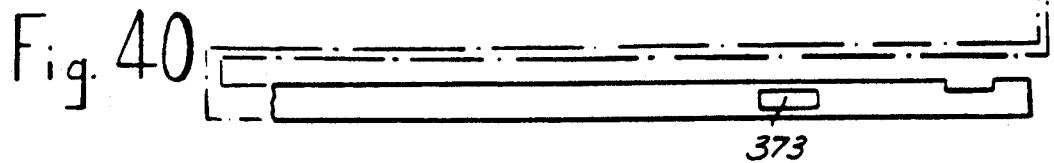
Fig. 32
Fig. 31
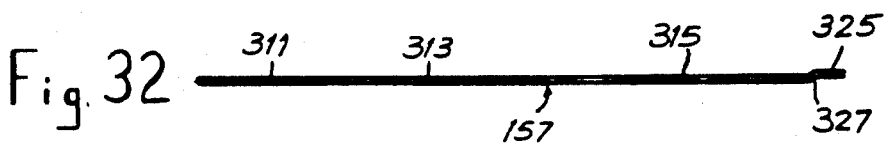
Fig. 28
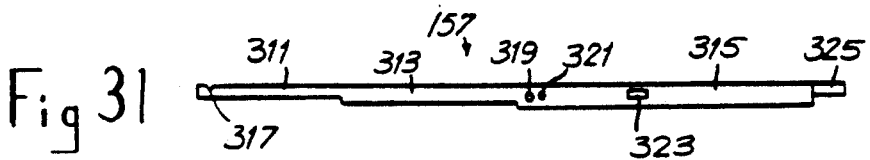
Fig. 29
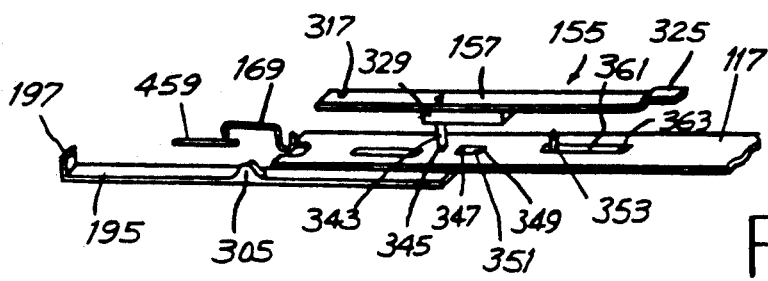
Fig. 37

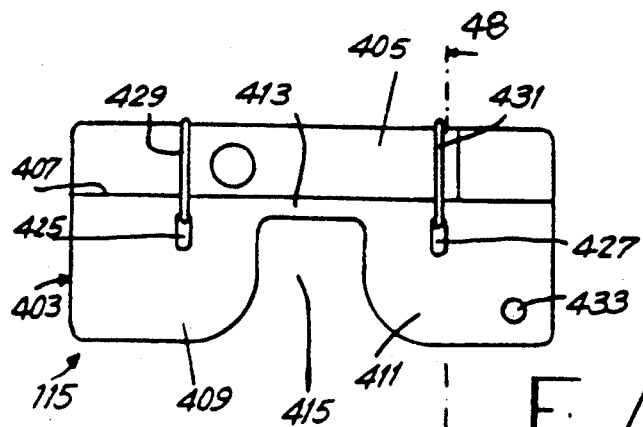
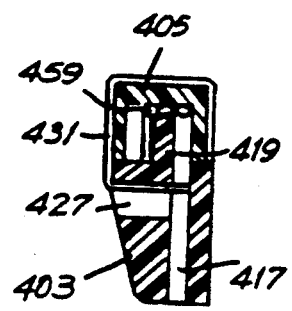
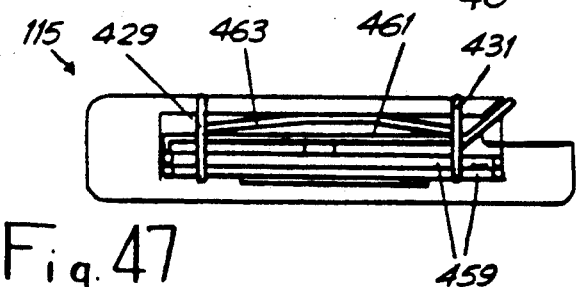
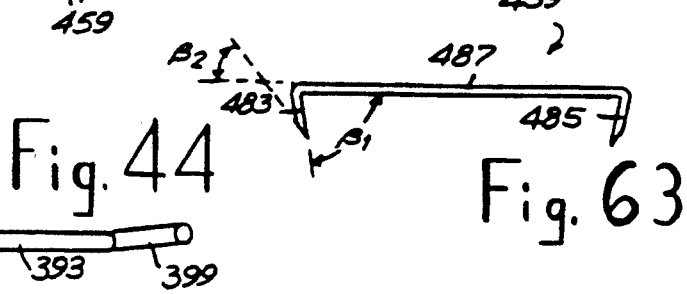
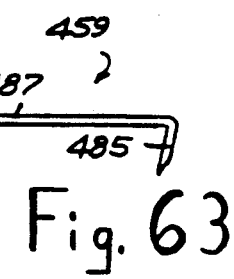
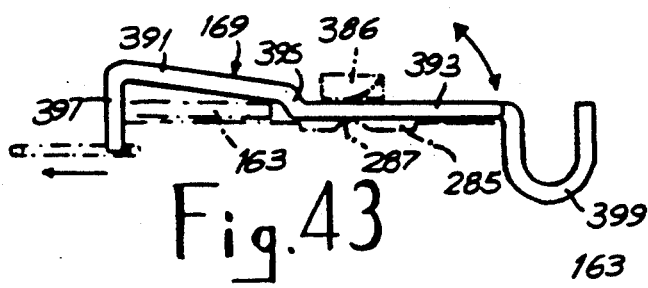
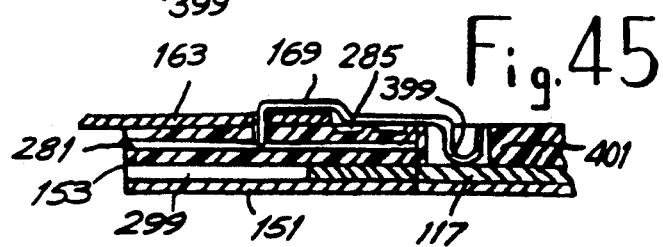

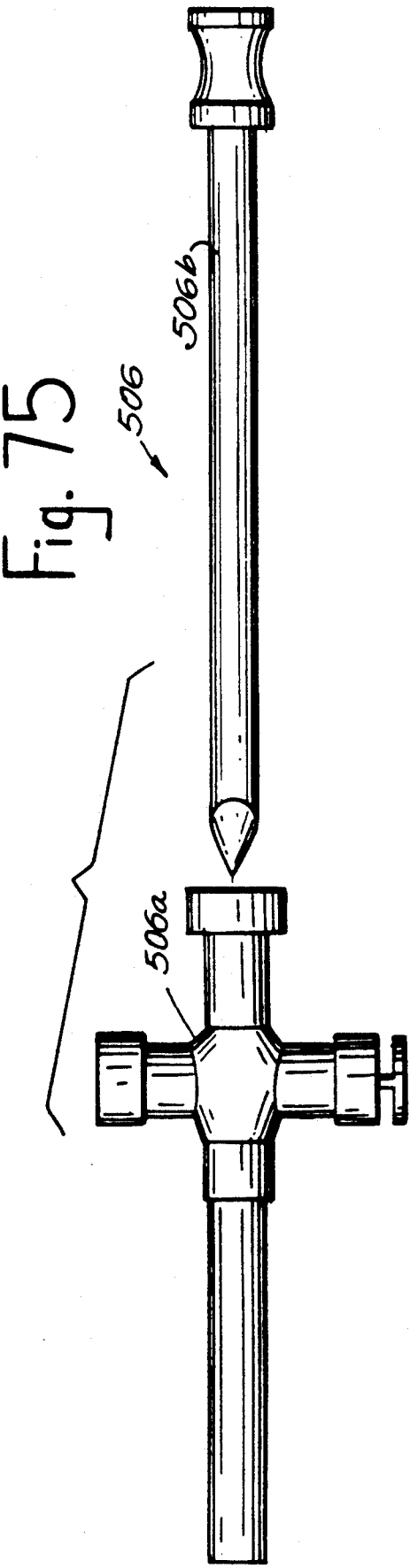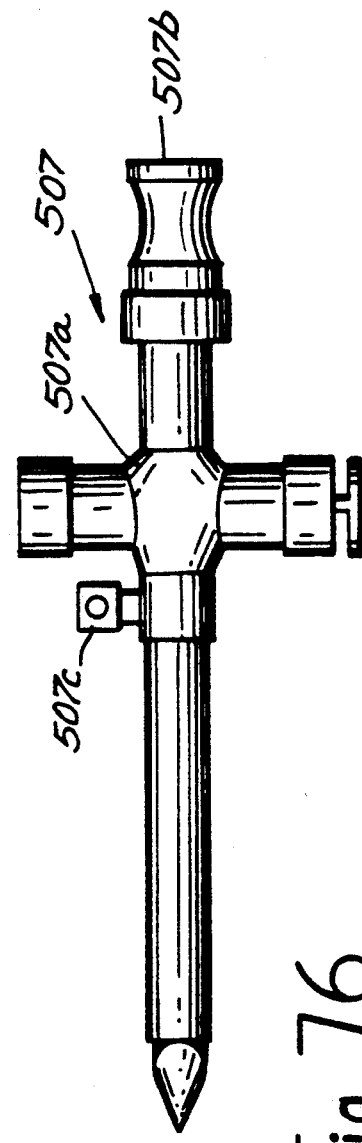

SURGICAL PROCEDURE FOR JOINING TISSUE IN AN INTERNAL BODY CAVITY

This application is a division of application Ser. No. 07/493,046 filed Mar. 12, 1990, (abandoned) which (now U.S. Pat. No. 5,125,553) is a continuation-in part of application Ser. No. 07/341,155, filed Apr. 20, 1989, a continuation-in-part of application Ser. No. 07/185,054, filed Apr. 22, 1988, and a continuation-in-part of application Ser. No. 07/195,586, filed May 18, 1988 (now U.S. Pat. No. 4,944,443). Application Ser. No. 07/341,155 is a continuation-in-part of application Ser. No. 07/185,054. Application Ser. No. 07/195,586 is a continuation of application Ser. No. 07/020,555, filed Mar. 2, 1987, now abandoned, which is a continuation of application Ser. No. 06/815,659, filed Dec. 30, 1985, now abandoned, which is a continuation of application Ser. No. 06/525,125, filed Aug. 22, 1983, now abandoned. The disclosures of U.S. Pat. Nos. 4,944,443 and 4,919,152, are incorporated herein by reference.

BACKGROUND OF THE INVENTION

This invention relates to apparatus and a method for joining, e.g. by stapling or clipping, internal body tissue from outside the body through a small opening in the body. The invention is useful for closing an internal opening in a body cavity from within the body cavity, such as in performing corrective surgery for hernias. More particularly, the invention relates to a procedure and apparatus for the minimally invasive repair of indirect inquinal or femoral hernias utilizing insufflation and laparoscopy.

The problem of herniation is one that may be experienced by men, women and children and generally relates to the abnormal protrusion of an organ or part of an organ or a portion of tissue through an aperture in its containing cavity. The usual, but not the only, hernia treated by this invention is congenital in origin, called an indirect inquinal hernia, and is due to the failure of the inner lining of the abdomen, called the peritoneum, to seal itself at the opening of the inquinal canal during fetal formation. The inquinal canal contains the spermatic cord. In its failure to seal itself, a hole develops with a sock shaped sac hanging downward from that hole. This sac rests inside the inquinal canal. This hole may allow a portion of intestine to slip through it and become pinched or even strangulated. It is necessary to close such an opening immediately or else complications may develop, such as strangulated intestines or in extreme case death.

There are several different traditional (prior art) surgical techniques for closing a hernial defect. All of these techniques have certain basic characteristics in common. Among these common characteristics is the necessity to make a formal 3 to 6 inch incision directly adjacent to the hernial defect which lies generally in the groin region, cutting and pealing back various layers of tissue and dissecting the inquinal canal and the accompanying spermatic cord in order to access the hernial defect at the mouth of the canal. Such procedures require 12 to 15 sutures to close the large and complicated incision. Obviously such procedures leave a rather large and sometimes unattractive scar and are extremely painful to the patient. Most patients are out of work an average of 5 days after such an operation and have restricted movement for over two weeks. More importantly the surgery carries a long list of both general and local complications such as ischemic orchitis and testicular atrophy caused by the dissecting of the spermatic cord off the hernial sac. One of the major problems with current procedures is recurrent herniation. It is estimated that as many as 20% of these procedures recur within 5 to 10 years. One reason for this is that current procedures damage the muscle tissue in the groin region which supports the inquinal area. This muscle tissue then weakens and bulges out due to the pressure of the intestines pushing this area down. Such muscle failure results in a direct inquinal hernia, the repair of which may require a synthetic mesh to reinforce the damaged muscle tissue.

Thus, the performance of such conventional corrective surgery causes severe physical trauma to the operative area and emotional trauma to the patient. Many other complications are possible: those related to any incision, such as bleeding and infection, and those related to conventional hernia procedures, such as damages to bowel and bladder, nerves and large blood vessels. In addition, cutting through so many layers of tissue may severely traumatize the tissue and upset the patient's emotional equilibrium. Other disadvantages of conventional hernia surgery are the long recuperation time and the large unsightly scar.

OBJECTS OF THE INVENTION

An object of the present invention is to provide apparatus and a method for joining, e.g. by stapling or clipping, internal body tissue through a small opening, e.g., with the aid of a laparascope.

Another object of the present invention is to provide apparatus and a method for performing corrective surgery on internal wounds such as hernias where invasion of the patient's body tissues is minimized and resultant trauma is reduced.

Another more particular object of the present invention is to provide such apparatus and method which do not require a formal incision or which minimize the size of the opening in the patient's body tissues.

Yet another particular object of the present invention is to provide in hernia cases apparatus and method for performing corrective surgery in which handling of a patient's scrotum and contents is avoided.

Another object of the present invention is to provide apparatus including a surgical instrument that can be inserted into the body cavity of the patient through a site on the patient's body remote from the wound.

A further particular object of the present invention is to provide such apparatus and method wherein the surgical operation is performed from within the body cavity of the patient, i.e., on the inner side of the hernia.

SUMMARY OF THE INVENTION

According to the invention, a method and apparatus are provided for joining, e.g. by stapling or clipping, body tissue, particularly internal body tissue reached through a small opening such as a trocar puncture. The method and apparatus are particularly useful for stapling body tissue to close an opening in a body wall. For example, the invention is useful for closing an opening in an internal body cavity through a small opening made into the body cavity.

The method and apparatus thus may close an opening such as a hernia in a body cavity such as the abdominal cavity from within the body cavity through a small opening into the cavity, as opposed to form outside the body cavity.

While the invention is described in more detail herein in connection with repair of a hernia, the invention is not limited to use only in the repair of a hernia, but may, for example, be used to close the lumen of a vessel or join together tissue in reconstructive surgery.

A method for joining body tissue in an internal body cavity, for example, tissue defining an opening such as a hernia in the abdominal cavity of a patient, comprises, in accordance with the present invention, the steps of (a) making a small opening (incision or puncture) into the body cavity at a site on the patient's body remote from the tissue to be joined, (b) inserting an elongate instrument through the small opening, and (c) moving the instrument through the small opening and through the body cavity so that the distal end of the instrument is close to the tissue to be joined and on the internal side of tissue in the body cavity. In another step, the two pieces of body tissue are gripped, for example, on opposite sides of the opening, approximated and held together, the step of gripping occurring from the internal side of the tissue in the body cavity. The composite step of gripping, approximating and holding is performed with the instrument by manipulation, e.g. manually, at a proximal end thereof. In another step of the method in accordance with the present invention, the two pieces of body tissue are joined together by a surgical device such as a staple or clip, this step being performed from the internal side of the tissue in the body cavity by manipulation of the instrument at a proximal end thereof.

According to a specific embodiment of the invention, a procedure and apparatus are provided for repairing hernias, e.g., closing the neck of the hernial sac, intra-abdominally by means of conventional insufflation and with the aid of a conventional operating laparascope. A salient aspect for the present invention is that it obviates a major operation with all the major and minor complications accompanying such a procedure, including ischemic orchitis and testicular atrophy and replaces it with a minor operation whose openings are limited to only small puncture wounds, e.g., about ½" or less, which are less damaging to muscle tissue and less painful to the patient than formal incisions. These small puncture wounds are inserted in the upper abdominal region, above the scarpia's fascia, in the area surrounding the navel, lateral to the navel, with the puncture for the surgical apparatus being on the same side as the hernia and remote to the hernial area so as not to damage the muscle tissue which supports the hernial defect.

A procedure in accordance with the invention for intra-abdominally repairing a hernia comprises conventionally insufflating the abdomen; inserting a cannula into the abdomen which provides a selectively sealable opening into the abdomen through which a stapling instrument may be introduced into the abdomen, the cannula providing a fluid-tight ("fluid-tight" as used herein means gas-tight and liquid-tight) seal between it and the stapling instrument inserted therethrough and the cannula providing a seal between it and tissue defining the opening into the abdomen, the seals being effective to substantially maintain insufflation of the abdomen; providing the stapling instrument with a fluid-tight internal seal effective to substantially maintain insufflation of the abdomen; inserting the stapling instrument into the abdomen through the cannula; and stapling body tissue with the stapling instrument adjacent to the hernial opening to repair it. A laparoscope is inserted into the abdomen via a similar cannula and fluid-tight seal to aid with the procedure Both the laparoscope and instrument are inserted into the abdomen remote from the hernial area above the scarpia's fascia.

A preferred embodiment of the procedure according to the invention is as follows In accordance with conventional laparoscopic procedures, the abdomen is insufflated conventionally using a conventional insufflator (e.g. $CO_2$) and a conventional Veress needle. A puncture wound is made with a small trocar and cannula, e.g., about ½" in diameter or less. When the trocar is removed from the cannula, the cannula valve seals and maintains pressure inside the insufflated abdomen. Another small trocar and cannula are used to make another small puncture wound, and the trocar is then removed. As mentioned above, both puncture wounds are made remote from the hernial area. An operating laparoscope is inserted through one of the two cannulas and is used to locate the hernial orifice and view the entire procedure intra-abdominally. A stapling instrument according to the invention is inserted into the insufflated abdomen through the other cannula. The instrument is long enough to reach the hernial defect from the point of the opening (puncture) (lateral to the navel). The stapling instrument has an inner pressure seal to keep gas from escaping from the insufflated abdomen and is shaped so as to seal when slid into the cannula. The stapling instrument is then operated to repair the hernia. One of the cannulas includes a gas port which is used to maintain gas pressure during the procedure.

The surgical instrument, for stapling interior body tissue from inside the body of the patient, in accordance with the invention comprises: tissue griping means for gripping the interior body tissue to be stapled; stapling means for stapling the interior body tissue with a surgical staple; actuating means for activating the tissue gripping means and the stapling means including first and second activators and movable means coupling the first and second activators with the tissue griping means and the stapling means, respectively; elongate frame means enclosing at least a substantial part of the coupling means, the coupling means being movable relative to the frame means; and means for sealing fluid-tight within the frame means one side of the frame means on which the tissue gripping means and the stapling means are disposed from another side of the frame means on which the activators are disposed, while permitting movement of the coupling means relative to the frame means.

The surgical instrument according to the invention has an elongated tubular section (frame means) which encloses and houses elongated rod-like and/or bar-like elements (movable coupling means) which engage and activate a stapling or stapling means and a pair of forceps at the end of the instrument. When activated the elongated elements open and close these forceps and can activate the stapling means. The forceps are used to pierce and hook the peritoneum directly adjacent and on both sides of the hernial orifice. The forceps then close the orifice and draw the peritoneum edges of the orifice into the stapling both sides of the closed orifice together creating a high ligation of the hernial sac. The instrument utilizes stainless steel staples or may utilize staples made of materials that the body absorbs, such as PGA.

The advantages of this procedure are many and include the advantage of not damaging the supporting muscle tissue in the hernial area so as to reduce recurrence. Another advantage includes leaving the spermatic cord in place so as to reduce the complication of ischemic orchitis and testicular atrophy. Another advantage includes substantially less pain to the patient and less scar tissue. Another advantage includes a faster recovery for the patient with less time lost from work. Another advantage includes substantially less operative time, usually one fourth the time it takes to perform current procedures. Another advantage includes using local anesthesia. Another advantage is that procedure according to the invention may be performed as an outpatient procedure and therefore is less costly to perform.

A surgical instrument for closing an opening, particularly a hernia, in the internal body wall of a patient from within the body cavity of the patient comprises, in accordance with the present invention, an elongate frame or superstructure, a staple storage component on the frame for temporarily storing at least one staple, a staple forming and ejection assembly at least in part movably mounted to the frame for ejecting the staple from the staple storage into the body tissues of the patient and plastically deforming the staple from an open position to a closed position in which the staple holds together two pieces of body tissue on opposite sides of the opening In one embodiment of the present invention, the instrument further comprises a tissue positioning assembly separate from the staple forming and ejection assembly for gripping, approximating and temporarily holding together in a stapling position the two pieces of body tissue prior to and during a stapling operation. In approximating the two pieces of tissue, the positioning assembly juxtaposes the tissue edges to one another and ensures that the tissue pieces lie in the same plane. Preferably, the tissue positioning assembly is designed to hold the two pieces of tissue in compression during the stapling operation Proper approximation and tight pressing of the tissues against one another ensures a successful closure and reduces the chances of scarring.

In another embodiment of the present invention, the staple storage component includes an elongate staple cartridge rotatably mounted to the frame at a distal end thereof and a rotator assembly operatively connected to the cartridge for rotating the cartridge from an orientation aligned with the frame to a staple ejection orientation transverse to the frame. The rotator assembly is critical in allowing large staples to pass through a small opening in the abdominal wall.

A first actuator is at least in part movably mounted to the frame and connected to the staple forming and ejection assembly for moving at least a portion thereof, while a second actuator separate from the first actuator is provided for moving at least a portion of the tissue positioning assembly prior to the stapling operation, the second actuator being at least in part movably mounted to the frame and connected to the tissue positioning assembly.

Pursuant to another feature of the present invention, the cartridge includes a staple chamber and spring tines for preventing a staple from falling out of the chamber prior to a staple ejection operation. In addition, the cartridge is advantageously provided with an inlet opening, a biasing spring and a staple plate for enabling the reception and storage of additional staples by the cartridge subsequently to the stapling operation.

Pursuant to another feature of the present invention, the rotator assembly includes a rotator member slidably mounted to the frame for longitudinal motion therealong and a rotator link pivotably attached at one end to the cartridge and at an opposite end to the rotator member. The instrument further comprises a timing mechanism mounted to the frame for controlling the initiation and duration of motion of the rotator member. In a preferred embodiment of the present invention, the staple forming and ejection assembly includes an elongate plate element movably mounted to the frame, the timing mechanism including a slot formed in the elongate plate element and a pin on the rotator member coacting with the slot.

In accordance with further particular features of the present invention, the rotator assembly further includes a biasing spring for forcing the pin against the elongate plate element and coacting stop elements are provided on the rotator member and the frame for limiting a range of longitudinal motion of the rotator member and concomitantly limiting the range of rotational motion of the cartridge. Advantageously, the slot in the elongate plate element is formed with beveled ends and the pin on the rotator member has a substantially conically shaped free end, whereby the pin is compelled to move transversely out of the slot upon an arresting of forward longitudinal motion of the rotator member by the coacting stop elements.

The coacting stop elements may include a floating in a direction transverse thereto, a shoulder at a proximal end of the rotator member and an additional slot in the elongate plate element, the additional slot being formed with a beveled proximal end and the floating pin being provided with conically shaped ends. In such a motion limiting structure, the floating pin is forced in a camming type motion transversely out of the slot upon an engagement of the floating pin with the beveled proximal end of the additional slot during relative motion of the elongate plate element and the rotator member after termination of a cartridge rotation operation. As a result of the transverse motion, the floating pin is shifted into a locking engagement with the shoulder of the rotator member.

Pursuant to an additional feature of the present invention, the staple forming and ejection assembly includes an anvil member with an anvil flange projecting, during the stapling operation, into a staple forming plane intersecting the cartridge. The surgical instrument further comprises a shifting mechanism for moving the anvil flange away from the staple forming plane prior to a cartridge rotation operation. Preferably, the anvil member is an elongate member with a proximal end attached to the frame and a distal end carrying the anvil flange, the shifting mechanism including a camming projection on the anvil member engageable with the plate member of the staple forming and ejection assembly.

Pursuant to yet another feature of the present invention, the frame carries a staple storage magazine in addition to the staple storage cartridge. A loading mechanism is provided for shifting additional staples from the storage magazine into the cartridge, and a staple arrest device is attached to the frame for preventing motion of staples from the magazine into the cartridge during a cartridge rotation operation and the stapling operation. The staple magazine preferably takes the form of an elongate chamber in the frame and the loading mechanism includes a compression spring. Moreover, the staple arrest device includes a pivotably mounted catch member having a camming portion engageable with the plate element.

In accordance with yet a further feature of the present invention, the tissue positioning assembly includes a pair of tong-like gripper members mounted to the frame for longitudinal motion therealong and a camming element for changing the distance between the tong-like gripper members during motion thereof so that during a closing stroke the tissue positioning assembly simultaneously draws two pieces of body tissue together and towards the staple cartridge. Preferably, the second actuator is mechanically connected to the tong-like gripper members and is spring biased for urging the tong-like gripper members towards a closed configuration. The tong-like gripper members are advantageously provided with collar-like elements for limiting the degree that the tong-like gripper members may be inserted into the body tissues of a patient and for ensuring the alignment of the tissue pieces in the same plane during an approximating operation.

Pursuant to another feature of the present invention, a staple-storing cartridge at a distal end of the suturing instrument is rotated upon insertion of the instrument through the small opening into the body cavity. The step of rotating is being accomplished via manual manipulation at the proximal end of the instrument.

The composite step of gripping, approximating and holding advantageously includes the steps of inserting ends of tong-like gripper members into the two pieces of tissue and moving the tong-like gripper members towards one another and towards the distal end of the stapling instrument. The tissue surface when inflated presents a generally concave surface to the instrument. The tong-like gripper members include structure which pierces the tissue to grip it, thus preventing the tissue from "walking away" from the tongs when they pierce the tissue. The composite step of gripping, approximating and holding is accomplished by manipulation of a first mechanism of the instrument, including the tong-like gripper members, and the step of stapling is accomplished by manipulation of a second mechanism of the instrument separate and distinct from the first mechanism.

Pursuant to yet another feature of the present invention, the distal end of a laparoscope is inserted into the body cavity to provide for visual inspection of the internal opening and the distal end of the instrument during a stapling operation. The laparoscope may be inserted through an external opening in the body wall of the patient different from the external opening through which the stapling instrument is inserted.

The stapling instrument and the surgical method in accordance with the present invention minimize the number and size of openings necessary to effect hernial repair, thereby greatly reducing the physical and emotional trauma of hernia patients. The openings are made at a distance from the site of the hernia, which further decreases the trauma to that area. Because of the substantial reduction in trauma, as well as a corresponding decrease in complications, patients operated on with an instrument in accordance with the present invention can walk away from the hospital an hour after surgery. In contrast, patients treated with conventional procedures must remain hospitalized for days, or longer in cases where complications arise.

It is to be noted that the rotatability of the staple cartridge enables the alignment of the cartridge with the longitudinal axis of the instrument and concomitantly enables an insertion of the narrow side of the cartridge first through the external opening, thereby decreasing the minimum required size of the opening. The rotatability of the staple cartridge thus allows the use of larger staples without an increase in the size of the opening through which the surgical instrument is inserted.

Other advantages of the present invention include the possibility of using a local anesthetic rather than a general anesthetic, an increase in the efficiency and ease of the operation and a concomitant reduction in support staff and operating time.

BRIEF DESCRIPTION OF THE DRAWINGS

FIG. 1 is a partially schematic side elevational view, on a reduced scale, of a surgical instrument in accordance with the present invention for suturing an opening, particularly a hernial tear, in internal body tissues of a patient, showing a staple cartridge in a longitudinal or aligned orientation.

FIG. 2 is a side elevational view similar to FIG. 1, showing the staple cartridge in a rotated orientation.

FIG. 3 is a side elevational view, on an enlarged scale, of the surgical instrument of FIGS. 1 and 2.

FIG. 4 is a view similar to FIG. 3, showing the surgical instrument rotated 90° about a longitudinal axis.

FIG. 5 is a side elevational view of an actuator lever on a handle, portion of the instrument of FIGS. 1-4.

FIG. 6 is a front elevational view of the actuator lever of FIG. 5.

FIG. 7 is a top view, on an enlarged scale, of a tissue positioning assembly shown in part in FIGS. 2 and 4.

FIG. 8 s a top view, on a larger scale, of a housing component of the tissue positioning assembly of FIG..7.

FIG. 9 is a cross-sectional view taken along line 9—9 in FIG. 8.

FIG. 10 is a partial longitudinal cross-sectional view taken along line 10—10 in FIG. 8.

FIG. 11 is a top view, on a substantially enlarged scale, of a tong like gripper member shown in FIG. 7.

FIG. 12 is a side elevational view of the tong-like gripper member sown in FIG. 11

FIG. 13 is a side elevational view of a cover plate included in the tissue positioning assembly of FIG. 7.

FIG. 14 is a top view, on a reduced scale, of a tissue positioning assembly actuator rod shown in part in FIGS. 3 and 7.

FIG. 15 is a side elevational view of the actuator rod of FIG. 14.

FIG. 16 is a bottom view, on an enlarged scale, of a channel member partially illustrated in FIGS. 3 and 4.

FIG. 17 is a side elevational view of the channel member of FIG. 16, taken from below in that drawing figure.

FIG. 18 is a top view of the channel member of FIGS. 16 and 17.

FIG. 19 is a side elevational view of the channel member of FIGS. 16-18, taken from below in FIG. 18.

FIG. 20 is a top view, on an enlarged scale, of a plastic body member partially illustrated in FIGS. 3 and 4.

FIG. 21 is a side elevational view of the plastic body member of FIG. 20, taken from above in that drawing figure.

FIG. 22 is a side elevational view of the plastic body member of FIG. 20, taken from below in that drawing figure.

FIG. 23 is a cross-sectional view taken along line 23—23 in FIG. 20.

FIG. 24 is a cross-sectional view taken along line 24—14 in FIG. 20.

FIG. 25 is a cross-sectional view taken along line 25—25 in FIG. 20.

FIG. 26 is a cross-sectional view taken along line 26—26 in FIG. 20.

FIG. 27 is a perspective view, on an enlarged scale, of a portion of the surgical instrument at a distal end thereof.

FIG. 28 is a top view, on an enlarged scale, of an anvil member shown in FIG. 4.

FIG. 29 is a side elevational view of the anvil member of FIG. 28.

FIG. 30 is a perspective view of a distal end of the channel member of FIGS. 16–19, showing the anvil member of FIGS. 28 and 29 attached thereto.

FIG. 31 is a top view of a rotator member depicted in FIGS. 3 and 27.

FIG. 32 is a side elevational view of the rotator member shown in FIG. 31.

FIG. 33 is a top view, on an enlarged scale, of a spacer element attached to the rotator member of FIGS. 31 and 32.

FIG. 34 is a side elevational view of the spacer element of FIG. 33, taken from below in that drawing figure.

FIG. 35 is another side elevational view of the spacer element of FIG. 33, taken from above in that figure.

FIG. 36 is a rear elevational view of the spacer element of FIG. 33, taken from the right in that figure.

FIG. 37 is an exploded perspective view, showing the relationship among the anvil member of FIGS. 28–30, the rotator member of FIGS. 31 and 32, a staple release lever shown in FIG. 3, and a staple forming and timing plate shown in FIGS. 1 and 3.

FIGS. 38 and 39 are partial longitudinal cross-sectional views, on an enlarged scale, illustrating operation of a floating locking pin shown in FIG. 37.

FIG. 40 is a top view of the staple forming and timing plate of FIGS. 1, 3 and 37.

FIG. 41 is a top view, on an enlarged scale, of a cover plate shown in FIGS. 3 and 4.

FIG. 42 is a side elevational view of the cover plate of FIG. 41.

FIG. 43 is a side elevational view, on an enlarged scale, of the stale release lever shown in FIGS. 3 and 37.

FIG. 44 is a top view of the staple release lever of FIG. 43.

FIG. 45 is a partial longitudinal cross-sectional view showing the structural relationship among the staple release lever of FIGS. 43 and 44, the staple forming and timing plate of FIGS. 1, 3, 37 and 40, the channel member of FIGS. 16–19 and 30, the plastic body member of FIGS. 20–22 and the cover plate of FIGS. 3 4, 41 and 42.

FIG. 46 is a top view, on an enlarged scale, of the staple cartridge of FIGS. 1–4, showing a first and a second cartridge body potion joined together.

FIG. 47 is a side elevational view of the first cartridge body portion of FIG. 46, showing a pair of staple holding springs and a stack of surgical staples.

FIG. 48 is a cross-sectional view taken along line 48—48 in FIG. 46.

FIG. 53 is a side elevational view, on an enlarged scale, of the first cartridge body portion of FIG. 46, taken from above in that figure.

FIG. 54 is a top view of the first cartridge body portion of FIG. 46, with the staple holding springs of that figure removed.

FIG. 55 is a side elevational view of the cartridge body portion of FIG. 54, taken from below in that figure.

FIG. 56 is an end elevational view of the cartridge body portion of FIG. 53, taken from the left in that figure.

FIG. 63 is an elevational view, on an enlarged scale, of a surgical staple in accordance with the present invention.

FIG. 64 is a partial view of a distal end of the staple forming and timing plate of FIG. 40 in engagement with a surgical staple at the onset of a staple forming or bending operation.

FIG. 65 is a view similar to FIG. 64, showing a later stage during the staple bending operation.

FIG. 66 is a view similar to FIGS. 64 and 65, depicting the completion of the staple bending operation.

FIG. 75 is an exploded perspective view of a conventional cannula and trocar used in the procedure illustrated in FIG. 74.

FIG. 76 is a perspective view of a conventional cannula and trocar with a gas stopcock used in the procedure illustrated in FIG. 74.

DETAILED DESCRIPTION

Figure 3A:
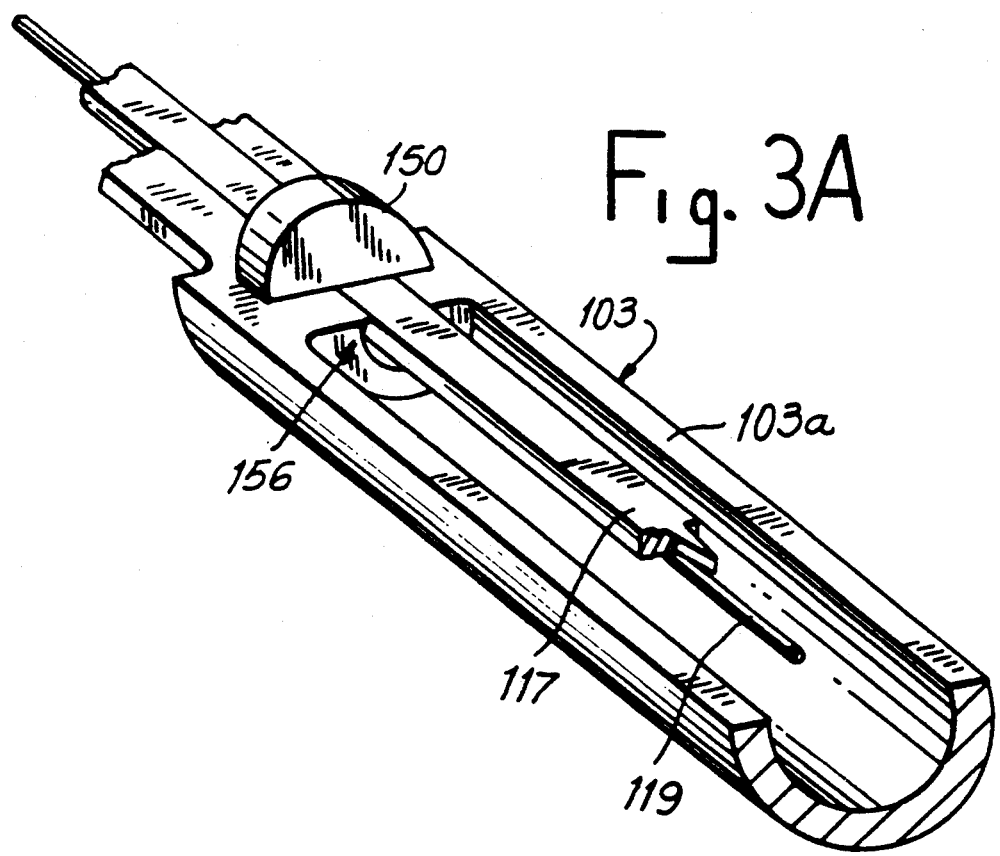
FIG. 3A is a perspective view of part of the surgical instrument of FIGS. 1-3, partially disassembled, showing an internal seal depicted in FIG. 3.

As illustrated in FIG. 1, a surgical instrument for suturing an opening such as a hernial tear in internal body tissues of a patient comprises an elongate frame 101 including a cylindrical handle portion 103, a handle extension 105 integral with handle portion 103, and a narrow superstructure assembly 107 inserted in and attached to handle portion 103 and extension 105. Handle portion 103 carries a first slidable button 109 for cocking the instrument, i.e., putting the instrument into a prefiring configuration, and a second slidable button 111 diametrically opposed to the first button for operating a tissue positioning assembly 113 shown in FIG. 2. First button 109 is mechanically coupled to a staple storing cartridge 115 via an elongate staple forming and timing plate 117 (FIG. 1), while second button 111 is operatively connected to tissue positioning assembly 113 via a gripper actuating rod 119 (FIG. 2). Handle portion 103 also carries an actuator lever 120 which is operatively linked to staple forming and timing plate 117 for shifting that element to bend a staple around an anvil, as described in detail hereinafter.

FIG. 2 shows the prefiring configuration of the instrument, i.e., the configuration immediately prior to a pivoting of actuator lever 120. Button 109 is disposed in a forward position and staple storing cartridge 115 has been rotated from an aligned or longitudinal orientation shown in FIG. 1 to a transverse staple firing orientation. FIG. 2 illustrates in dashed lines a forward position of button 111 and a concomitant extended configuration of tong-like gripper members 121 and 123, the gripper members 121 and 123 being poised for gripping two pieces of body tissue on opposite sides of a hernial opening.

Figure 3B:
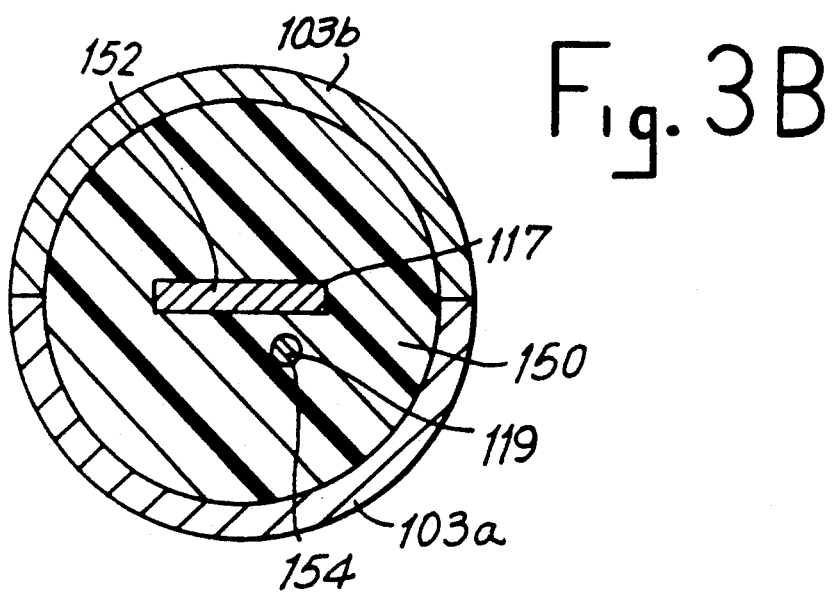
FIG. 3B is a cross-section taken through the seal of FIG. 3A with the handle assembled.
Figure 49:
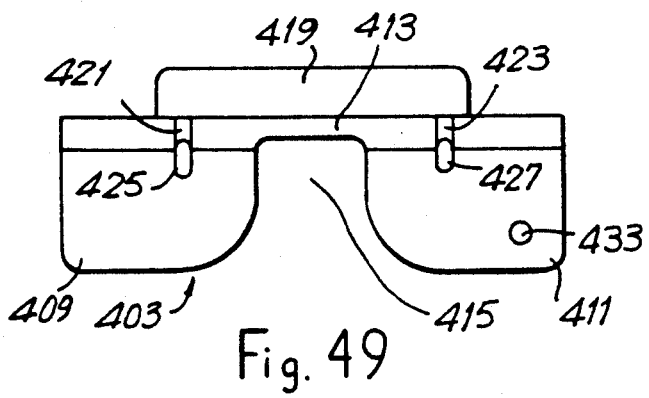
FIG. 49 s a top view, on an enlarged scale, of the second cartridge body portion of FIG. 46.

As depicted in FIG. 3, button 109 is formed with a planar projection 125 traversing a longitudinal and radial slot 127 in handle portion 103 and connected to a proximal end of staple forming and timing plate 117. Projection 125 is provided with one or two longitudinally extending arms 129 disposed in a longitudinal and circumferential slot 131 in handle portion 103 for bracing slidable button 109. The proximal end of staple forming and timing plate 117 is connected to handle portion 103 via a tension spring 133 which biases the plate element towards the proximal end of the instrument.

Button 111 is similarly formed with a planar projection 135 traversing a longitudinally elongate radial slot 137 in handle portion 103 and connected to a proximal end of actuator rod 119. Like projection 125 of button 109, projection 135 of button 111 is provided with one or two longitudinally extending arms or fins 139 disposed in a longitudinal and circumferential slot 141 in handle portion 103 for bracing slidable button 111. The proximal end of actuator rod 119 is connected to a tension spring 143 in turn connected to handle portion 103, whereby actuator rod 119 is biased towards the proximal end of the instrument.

Handle portion 103 is provided with a detent element 145 mounted on the handle via a leaf spring member 147. Detent 145 is engageable with a proximal edge of the rearward arm of fin 129 for preventing, upon the attainment of the prefiring configuration by the instrument, proximal motion of plate element 117 and concomitantly button 109 in response to the force exerted by tension spring 133. Detent 145 is disengageable from the rearward arm or fin 129 by manual pushing of a release button 149 slidably disposed in handle or housing 103.

Plate element 117, and activator rod 119, pass through and are sealed within handle portion 103 by sealing disc 150 (FIG. 3) made of flexible and fluid- (gas and liquid) impermeable material such as silicone rubber, polypropylene, polyethylene, etc. Holes 152 and 154 (FIG. 3B) in sealing disc 150 are shaped to correspond to plate 117 and rod 119 and sized to form a seal about plate 117 and rod 119 while permitting plate 117 and rod 119 to slide through the respective holes. Retainer structure referenced generally by 156 receives disc 150 and retains it against axial movement within handle portion 103. Disc 150 is provided with a diameter slightly larger than the inner diameter of handle 103 adjacent retainer structure 156 so as to provide an interference fit of disc 150 in assembled handle portion 103 (FIG. 3B) and a fluid-tight seal between the outer periphery of disc 150 and the inner periphery of handle portion 103. Handle portion 103 includes upper 103a and lower 103b parts which are sealed, e.g., ultrasonically, to seal handle portion 103. Sealing the interior of handle portion 103 with respect to plate 117 and rod 119 enables instrument 101 to be used in an insufflated body cavity, as described, for example, in connection with FIGS. 74-76 and the hernial repair procedure according to the invention.

Superstructure assembly 107 comprises two principal structural components: an elongate channel member 151, shown in detail in FIGS. 16-19, and a cooperating elongate plastic body member 153, shown in detail in FIGS. 20-22. Superstructure assembly 107 carries a rotator assembly 155 including a rotator member 157, which is engageable by staple forming and timing plate 117, and a rotator link 159 pivotably attached at a proximal end to rotator link 159 pivotably attached at a proximal end to rotator member 157 and at a distal end to a corner of staple cartridge 115. As explained in detail hereinafter with reference to FIGS. 37 and 67-72, the rotator assembly is responsive to a portion of the forward or distal motion of plate 117 to rotate cartridge 115 from an aligned or longitudinal orientation shown in FIG. 1 to a transverse staple firing orientation shown in FIG. 2. Rotator member 157 carries a slidably mounted rotator pin 343 (FIGS. 37 and 67-73) held against staple forming and timing plate 117 by a leaf spring 161.

Superstructure assembly 107 further comprises a cover plate 163 to a distal end of which the staple cartridge 115 is hingedly secured via a pivot pin 165. Cover plate 163 is provided with a cutout 167 through which a staple release lever 169 passes. As described hereinafter, staple release lever 169 is engageable with staple forming and timing plate 117 to control shifting of additional staples to cartridge 115 from a staple magazine (not shown in FIG. 3) in superstructure assembly 107. Staple release lever 169 is biased towards an open or staple release position by a leaf spring 171 attached by an ultrasonic weld at 173 to plastic body member 153.

Superstructure assembly 107 carries a slidably mounted staple pusher 175 which shifts additional staples longitudinally along superstructure assembly 107 towards cartridge 115. Staple pusher 175 is forced towards the distal end of the instrument by a compression spring 177.

FIGS. 4 and 5 illustrate in side elevational view the actuator lever 120 of FIGS. 1 and 2. Actuator lever 120 has an outer profile line 179 designed to accommodate the fingers of a human hand and is hingedly secured via a pivot pin 181 to a pair of brackets 183 on handle portion 103. Actuator lever 120 is biased by a torsion spring 185 into an open or raised position shown in FIG. 4.

As illustrated in FIGS. 5 and 6, actuator lever 120 has a base portion 187 provided with a projecting lug 189 having a finger extension 191. Finger extension 191 traverses a slot 193 (FIG. 3) in staple forming and timing plate 117, whereby pivotal motion of actuator lever 120 causes a longitudinal motion of plate 117.

Additional components of superstructure assembly 107 illustrated in FIG. 4 include an elongate anvil member 195 having a proximal end attached to channel member 151 and a distal, free, end provided with a transversely extending anvil flange 197. As described hereinafter with reference to FIGS. 67-72, staple forming and timing plate 117 cooperates with anvil member 195 to shift anvil flange 197 in a transverse direction to prevent interference with the rotation of cartridge 115. FIG. 4 shows anvil member 195 in a shifted or bent configuration.

FIG. 4 also shows a tissue positioning assembly housing 199 fixed at a distal end to actuator rod 119 and having a pair of outwardly turned flanges 201 (only one visible in FIG. 4) slidably grasped by inwardly turned fingers 203 on channel member 151. The entire tissue positioning assembly 113 shifts longitudinally in response to motion of actuator rod 119.

Tissue Positioning Assembly

Tissue positioning assembly 113 is shown in greater detail in FIGS. 7-15. Tissue positioning assembly housing 199 takes the shape of a channel with flanges 201 disposed along an open side of the channel (FIG. 9). The housing has a base portion 205 with two different thicknesses at opposite ends. At a distal end, the base portion is provided on opposite longitudinally extending sides with a pair of elongate grooves 207 and 209 each terminating at a proximal end in a respective transversely extending groove 211 or 213. At a proximal end, base portion 205 of the tissue positioning assembly housing is similarly provided with an L-shaped groove 214 for receiving a hook-shaped distal end 215 (see FIG. 14) of actuator rod 119.

As depicted in FIGS. 7, 11 and 12, tong-like gripper members 121 and 123 are provided at their proximal ends with inwardly turned tips 217 and 219. Proximal portions of gripper members 121 and 123 are received in grooves 207 and 209 in housing base 205, inwardly turned tips 217 and 219 being seated in transverse grooves 211 and 213, respectively. Upon a disposition of gripper members 121 and 123 in grooves 207 and 209 and a placement of the hook-shaped distal end 215 of actuator rod 119 in L-shaped groove 214, a cover plate 221, shown in side elevation in FIG. 13, is fitted into channel-shaped housing 199 over the gripper members and the hook-shaped distal end of actuator rod 119.

Tong-like gripper members 121 and 123 are each formed at a central location with a respective bent portion 223 and 225, whereby a forward or distal end of each gripper member is staggered inwardly, i.e., towards the body of superstructure assembly 107 and cartridge 115 (see FIG. 4).

The distal end portions of gripper members 121 and 123 take the form of outwardly bent fingers 227 and 229 having inwardly turned hooks 231 and 233. As described in connection with FIG. 74, hooks 231 and 233 pierce the tissue and hook it in a secure fashion so the tissue may be gripped and pulled. With the abdomen insufflated, the peritoneum directly adjacent and on both sides of the hernial orifice in the hernia procedure described herein presents a concave surface to the instrument distal end. This surface is under internal gas pressure to extend away from the approaching instrument. Hooks 23 a nd 23 pierce and grip the peritoneum surface and prevent the tissue from "walking away" from the instrument when fingers 227 and 229 are closed to grip the area surrounding the hernia. Fingers 227 and 229 of gripper members 121 and 123 are provided with respective collars 235 and 237 which serve as stops to limit the amount of tissue penetration by the fingers during a gripping operation and which ensure that the tissue pieces are aligned in the same plane during an approximating and a subsequent stapling operation.

Channel or Housing Member

As shown in FIGS. 16-19, channel member 151 includes an elongate base 239 and two longitudinally extending side walls 241 and 243 (FIG. 18) attached thereto. The inwardly turned fingers 203 (FIG. 4) for slidably supporting tissue positioning assembly housing 199 each include a first segment 245 located in the same plane as a respective side wall 241 or 243 and a second segment 247 extending inwardly from the free end of the respective first segment, second segment 247 being disposed in a plane parallel to and spaced from the plane of channel base 239. The tissue positioning assembly support fingers 203 are formed by punching them out of base 239 and then bending them into an L-shaped configuration, channel base 239 being formed in the process with a plurality of apertures 249 in regions about support fingers 203.

A leading channel part in the form of a plate-shaped bracket 251 is connected to the distal end of channel member 151 via an inclined bight 253. Bracket 251 and bight 253 are provided with a rectangular opening 255 flanked on an outer side of channel member 151 by a pair of longitudinally and outwardly extending lugs 257. Rectangular opening 255 is traversed by tong-like gripper members 121 and 123, while lugs 257 serve as camming posts for inducing a closing of tong-like gripper members 121 and 123 during a retraction stroke thereof in response to the biasing force exerted by tension spring 143 (FIG. 3).

Bracket 251 is formed at a leading edge with a rectangular recess 259 traversed by anvil flange 197 in an operational position thereof. Bracket 251 is also formed at its leading edge with a hole 261 which receives a pivot pin (see pin 437 in FIGS. 53 and 55) for the mounting of cartridge 115.

To facilitate the attachment of channel member 151 to plastic body member 153, side walls 241 and 243 are provided with a plurality of upstanding lugs 263 which are bent over plastic body member 153 during assembly. Side wall 243 is additionally provided with a pair of upstanding T-shaped locking projections 265 which mate with similarly shaped indentations 267 along a side of plastic body member 153 (see FIGS. 20 and 22).

PLASTIC BODY MEMBER

Plastic body member 153 is depicted in detail in FIGS. 20-26. That member, like other non-load-bearing components of the surgical instrument, is preferably made of a synthetic resin material such as medical grade polycarbonate. FIGS. 23, 25 and 26 show that plastic body member 153 has a flattened generally T-shaped cross section which accommodates side walls 241 and 243 of channel member 151 (FIG. 25).

As illustrated particularly in FIGS. 20 and 23, plastic body member 153 is provided at a distal end with a longitudinally extending recess 269 which serves as a guide or track for rotator member 157. Recess 269 has a relatively narrow forward portion 27 and a widened rearward portion 273, a shoulder 275 being located at the junction between the forward portion and the rearward portion of recess 269. Shoulder 275 serves as an abutment which limits the displacement of rotator member 157 in the distal direction.

Forward portion 271 of recess 269 communicates with a longitudinally oriented groove 277 which receives a tip of rotator link 159, while rearward portion 273 of recess 269 is interrupted by an elongate essentially rectangular cutout 279 in plastic body member 153.

As shown in FIGS. 21 and 23-25, plastic body member 153 is provided along one side with an elongate longitudinal slot 281 which is closed by side wall 241 of channel member 151 (FIG. 25) to form a staple magazine for holding additional staples prior to their loading into cartridge 115. Staple pusher 175 (FIG. 3) extends at least partially into slot 281 for pushing staples therealong and into cartridge 115. At a distal end, plastic body member 153 has a cylindrical bore 283 which communicates with magazine slot 281. As described in greater detail below with respect to FIGS. 43-45, staple release lever 169 has at a front end a transversely extending segment 397 which passes through bore 283 and extends into magazine slot 281 for preventing a forward advance of staples under the action of compression spring 177 and staple pusher 175.

The distal end of plastic body member 153 is further provided with a prismatic recess 285 (see FIGS. 20 and 24) traversed by a semicylindrical hump 287. Hump 287 serves as a support point for staple release lever 169 (FIGS. 3 and 4). Distally of recess 285, a cylindrical lug 288 projects from an upper surface of plastic body member 153 for facilitating the attachment of cover plate 163 (FIG. 3) to plastic body member 153. Proximally of recess 285, a prismatic lug 289 projects from plastic body member 153 for enabling the attachment of leaf spring 171 to plastic body member 153. An upper surface of prismatic lug 289 is welded ultrasonically to leaf spring 171, as mentioned above.

One edge of plastic body member 153 is provided along a proximal half with a series of longitudinally spaced, transversely oriented indentations 291 defined in part by respective ledges 293. Indentations 291 receive respective lugs 263 (FIGS. 18 and 19) of channel member 151, the lugs being bent during an assembly operation to conform to the shapes of the indentations. The same edge of plastic body member 153 is formed with T-shaped indentations 267 for receiving T-shaped locking projections 265 on channel member 151.

Along a longitudinally extending side of plastic body member 153 opposite indentations 267 and 291, member 153 is provided with a plurality of longitudinally spaced, rectangular recesses 295 in which lugs 263 on channel side all 241 are disposed upon assembly of the instrument. On a proximal end portion of plastic body member 153 is attached a plate 297 which serves to secure compression spring 177 (FIG. 3).

FIG. 27 illustrates the distal end of superstructure assembly 107 with cover plate 163, anvil member 195 and bracket 251 removed. A rectangular space 299 is formed between base 239 of channel member 151 and a lower surface of plastic body member 153. That space houses staple forming and timing plate 117, as indicated in dot-dash lines in FIG. 25.

Anvil Member

Anvil member 195 (FIG. 4) is illustrated in detail in FIGS. 28 and 29. Anvil member 195 is basically an elongate metal strip having a narrow distal half 301 and a wider proximal half 303. Anvil flange 197 is disposed at the distal end of narrow strip half 301 which is further provided with a shallow bent U-shaped portion 302. Anvil member 195 carries at the distal end of wider strip half 303 a transversely extending semicircular camming projection 305. Projection 305 engages staple forming and timing plate 117 during a forward or distal motion thereof and thereby cooperates with that plate member to laterally bend anvil member 195 so that anvil flange 197 is removed, during a cartridge rotation operation, from engagement with cartridge 115 (see rest position of the anvil FIG. 3). As shown in FIG. 30, anvil member 197 is attached at a proximal end to channel member 151 via an ultrasonic or electrical spot weld 307. Camming projection 305 traverses a rectangular opening 309 in base 239 of channel member 151.

Rotator Assembly

The several components of rotator assembly 155 (FIG. 3) are shown in FIGS. 31-37. Rotator member 157 (FIGS. 31 and 32) is n elongate plate-shaped component having three contiguous portions 311, 313 and 315 of increasing width. The distal end of the most forward portion 311 is provided along ne edge with a semicircular recess 317 which is traversed by a leg (not illustrated) of rotator link 159. That rotator link leg extends through recess 317 and into groove 277, as discussed hereinabove with reference to FIG. 20. The third, widest, portion 315 of rotator member 157 is provided at a forward end with a pair of circular apertures 319 and 321 and a rectangular aperture 323. A finger 325 is connected via an inclined web 327 to the rearward or proximal end of rotator member 157. The purpose and function of finger 325 and inclined web 327 are explained hereinafter with respect to FIG. 37-39.

As shown in FIG. 37, rotator assembly 155 includes a spacer element 329 attached to a side of rotator member 157 facing staple forming and timing plate 117. The spacer element is depicted in detail in FIGS. 33-36. Spacer element 329 has an elongate prismatic body 331 with a pair of elongate flanges 333 and 335 in the form of cross-sectionally rectangular beads extending the length of spacer body 331. At a distal end, spacer body 331 is formed with a transverse cylindrical post or peg 337 and a circular hole 339, while at a proximal end, the spacer body has an upstanding prismatic post or peg 341. Cylindrical peg 337 mates with circular aperture 319 in rotator member 157 (FIG. 31), while prismatic peg 341 traverses rectangular aperture 323. To a free end of peg 341 leaf spring 161 (FIG. 3) is ultrasonically or electrically welded.

Rotator assembly 155 further includes a pin 343 (FIG. 37) which is slidably inserted through hole 339 of spacer element 329 and aperture 321 of rotator member 157. Pin 343 has a pointed or conical free end 345 which coacts with beveled ends 347 and 349 of a slot 351 in staple forming and timing plate 117 (FIGS. 37 and 40) to properly control and time the operation of rotator assembly 155. Prior to the commencement of a cartridge rotating operation, conical end 345 of pin 343 engages a surface of staple forming and timing plate 117, as indicated generally in the exploded view of FIG. 37, while the upper end of the pin projects through aperture 321 to slightly bend leaf spring 161 on an opposite side of rotator member 157.

Upon a forward motion of plate 117, pin 343 drops into slot 351 under the force exerted by spring 161, and conical pin end 345 contacts the beveled proximal end 349 of slot 351. The angles of inclination of conical end 345 and beveled end 349 and the associated coefficients of friction are such that rotator member 157 is entrained during continued forward motion of staple forming and timing plate 117. At the termination of a rotation operation, the distal end of spacer element 329 contacts shoulder 275 of plastic body member 153 (FIG. 20) and thereby stops the forward motion of rotator member 157. Upon the arrest of rotator member 157, pin 343 slides upwardly along beveled slot end 349 and is thus transversely displaced in opposition to the force exerted by leaf spring 161 so that, during further forward motion of staple forming and timing plate 117, conical pin end 345 slidingly engages a major planar surface of the staple forming and timing plate.

As illustrated in FIGS. 37, 38 and 39, rotator assembly 155 further includes a floating pin 353 slidably disposed in a transverse bore 355 in plastic body member 153. Floating pin 353 has a Conical first end 357 and a conical second end 359. Prior to the termination of a rotation operation by rotator assembly 155, conical end 357 of floating pin 353 traverses or is disposed in a slot 361 in staple forming and timing plate 117 (FIGS. 37-40). Upon an arrest of forward motion of the staple forming and timing plate by the contact between spacer element 329 and shoulder 275, conical pin end 357 cams against a beveled end 363 of slot 361, whereby pin 353 is transversely displaced in bore 355 so that, during further forward motion of staple forming and timing plate 117, conical pin end 359 is disposed in the plane of rotator member 157 and contacts inclined web 327 (FIG. 32) to lock rotator member 157 against rearward motion during a stapling operation. Finger 327 serves to prevent floating pin 353 from leaving slot 355.

As depicted in FIG. 40, staple forming and timing plate 117 has a distal end formed with a pair of longitudinally extending prongs 365 which define a rectangular recess 367. As described in detail hereinafter with reference to FIGS. 64-66, prongs 365 cooperate with anvil flange 197 to deform a surgical staple from an open configuration to a closed configuration. Staple forming and timing plate 117 is also provided at a distal end with a longitudinally extending slot 369 which enables the disposition of anvil flange 197 in the stapling plane upon the completion of a cartridge rotation operation. Two additional slots 371 and 373 in staple forming and timing plate 117 respectively serve to limit the motion of the staple forming and timing plate in both the distal and proximal directions and to receive finger extension 191 of actuator lever 120 so that the lever can move staple forming and timing plate 117 in the distal direction during a power stroke of a stapling operation.

Cover Plate

FIGS. 41 and 42 show in detail the structure of cover plate 163 (see FIGS. 3 and 4). The distal end of the cover plate is formed with a circular hole 375 receiving cartridge pin 165 (FIGS. 3 and 53-55), an aperture 377 for receiving cylindrical lug 288 (FIGS. 20-22), and another aperture 379 which is aligned with bore 283 for receiving a distal part of staple release lever 169. The distal end of cover plate 163 is further provided with a rectangular recess 381 for receiving a lug 263 on channel member side wall 241 upon a bending of the lug during assembly of the surgical instrument. A linear cut 378 extends longitudinally from the end of cover plate 163 to cutout 167, thereby separating the distal end of the cover plate into two parallel sections 383 and 385. Section 385 is bent to occupy a plane transversely staggered with respect to the plane of the other section 383 and the body of cover plate 163 (see FIG. 42). Cover plate 163 also has a rectangular opening 387 through which prismatic lug 289 of plastic body member 153 (see FIGS. 20-22) projects, while one side edge of cover plate 163 is formed at a proximal end with a large rectangular cutout 389 coextensive with cutout 279 on plastic body member 153.

As shown in FIG. 43, section 385 of cover plate 163 is provided with a laterally extending rectangular lug 386 which overlies staple release lever 169 and serves to hold that lever in position. The relationship between lug 386, staple release lever 169 and hump 287 of plastic body member 153 (see FIGS. 20 and 24) is depicted in FIG. 43. Lug 386 and hump 287 are disposed on opposite sides of the staple release lever and cofunction to limit the transverse displacement of and to form a fulcrum point for that member.

Staple Release Lever

Staple release lever 169 has two straight coplanar body segments 391 and 393 inclined with respect to one another and interconnected by a bight segment 395. At a distal end, body segment 391 is provided with a transversely extending leading segment 397 which passes through aperture 379 in cover plate 163 (FIG. 4) and bore 283 in plastic body member 153 (FIGS. 20 and 23), as pointed out above. At a proximal end, body segment 393 is integral with a U-shaped camming segment 399 which is bent slightly out of the plane of body segments 391 and 393 (FIG. 44).

As illustrated in FIG. 45, U-shaped camming segment 399 of staple release lever 169 is disposed in a prismatic recess 401 in plastic body member 153 (FIG. 20) and engages a surface of staple forming and timing plate 117 essentially during all motion thereof. However, prior to an initial forward motion of the staple forming and timing plate, i.e., prior to the cocking of the instrument by button 109 (FIGS. 1-3), U-shaped camming segment 399 extends into the rectangular space 299 defined by channel member 151 and plastic body member 153. In that neutral configuration of the instrument, leading segment 397 of staple release lever 169 does not traverse any part of magazine slot 281. Upon a pivoting of staple release lever 169 about hump 287 during an initial forward motion of staple forming and timing plate 117, leading segment 397 of the staple release lever enters magazine slot 281 to prevent passage of staples therealong.

The staple forming and timing plate moves forward, i.e., towards the distal end of the instrument, initially in response to the cocking movement of button 109 (see FIGS. 1-3). Upon the attainment by the instrument of a prefiring configuration and upon the manipulation of button 11 to grip new portions of internal body tissues, actuator lever 120 is then pivoted to provide a power stroke of staple forming and timing plate 117.

Staple Cartridge

As illustrated in FIG. 46, 47 and 48, staple cartridge 115 comprises a first body portion 403 and a second body portion 405 attached to one another by ultrasonic or electrical spot welding along a joint 407. First body portion 403, shown by itself in FIGS. 49-52, is generally U-shaped and has a pair of arms 409 and 411 connected by a bight portion 413. Arms 409 and 411 and bight portion 413 define a prismatic recess 415 in which anvil flange 197 is disposed during a stapling operation. Body portion 403 is further formed with an elongate slot 417 having a flattened T shape and extending through both arms 409 and 411, as well as bight portion 413. During deformation of a surgical staple into a closed configuration, staple forming and timing plate 117 passes through the central, wider portion of slot 417 and the bending of the staple around anvil flange 197 takes place at least partially in slot 417. Arms 409 and 411 accordingly extend from bight portion 413 to prevent a twisting of the staple during a staple forming operation prior to entry of the staple into the tissue.

On a side opposite arms 409 and 411, first body portion 403 of cartridge 115 is provided with a flat projection 419 which is inserted into second body portion 405 (see FIG. 48). First body portion 403 is additionally provided with a pair of grooves 421 and 423 which communicate with respective holes 425 and 427 in the body portion. The grooves and the holes receive portions of respective staple holding springs 429 and 431, illustrated in FIGS. 46-48. In addition, arm 411 of the first body portion 403 is formed in one corner with a cylindrical bore 433 which receives an end of rotator link 159 (FIGS. 3 and 4).

FIGS. 53-56 show in detail the structure of body portion 405 of cartridge 115. Body portion 405 takes basically an elongate prismatic shape provided on opposite sides with a pair of outwardly extending cylindrical lugs or pegs 165 and 437. As mentioned hereinabove, peg 165 is received in hole 375 of cover plate 163, while peg 437 is received in hole 261 on bracket 251 of channel member 151. Body portion 405 is also provided on opposite sides with two pairs of grooves 439, 441 and 443, 445 in which staple holding springs 429 and 431 are seated.

Cartridge body portion 405 defines a staple storing chamber 447 which communicates with an elongate passageway 449 through which staple forming and timing plate 117 moves during a stapling operation. One corner of body portion 405 is cut out to form a rectangular recess 451 which communicates with chamber 447 via a staple entrance gap 453 defined in part by two beveled surfaces 455 and 457.

Figure 57:
FIG. 57 is an elevational view of a staple holding spring of FIGS. 46–48.
Figure 67:
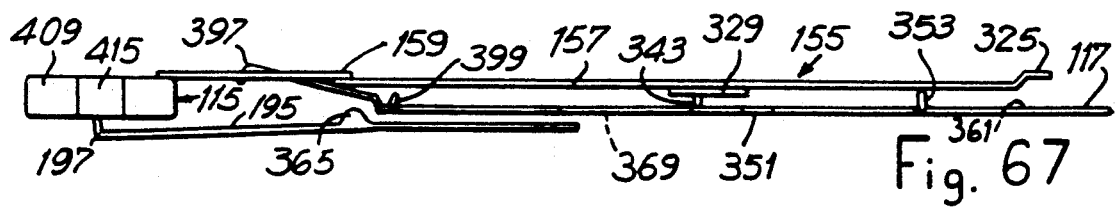
FIGS. 67-72 are diagrams illustrating successive steps in a cartridge rotation operation during which relative positions of selected components of a surgical instrument in accordance with the present invention change.

As depicted in FIGS. 47 and 48, staple holding springs 429 and 431 substantially surround cartridge body portion 405 and have portions extending transversely through cartridge 115 and across slot 417 to hold surgical staples 459 in cartridge 115. The portions of springs 429 and 431 which extend into slot 417 are bent outwardly, under force transmitted via staple forming and timing plate 117, to allow passage of a staple during a stapling operation. Staple holding spring 431 alone is illustrated in FIG. 57.

Figure 58:
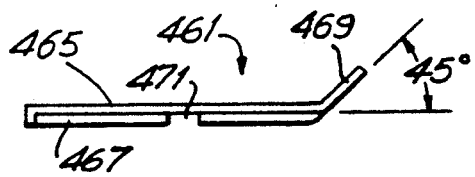
FIG. 58 is a side elevational view, on an enlarged scale, of a staple pusher shown in FIG. 47.
Figure 59:
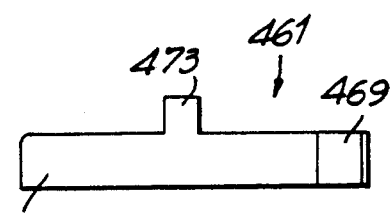
FIG. 59 is a top view of the staple pusher of FIG. 58.
Figure 50:
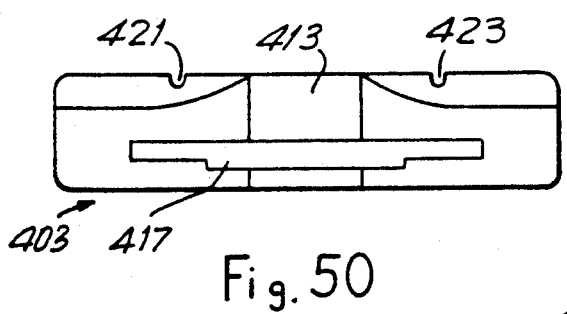
FIG. 50 is an elevational view of the cartridge portion of FIG. 49, taken from below in that drawing figure.
Figure 60:
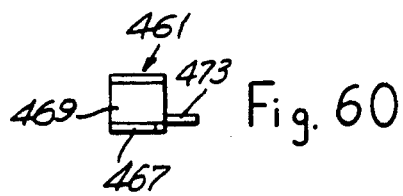
FIG. 60 is an end elevational view of the staple pusher of FIGS. 47, 58 and 59, taken from the right in FIG. 58.
Figure 51:
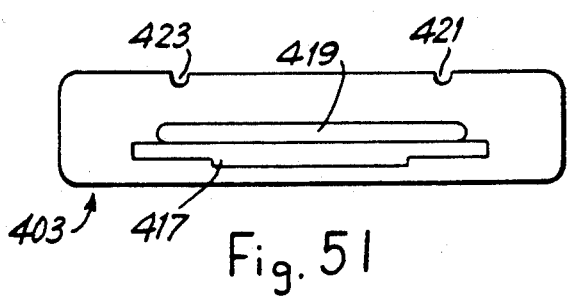
FIG. 51 is an elevational view of the cartridge portion of FIG. 49, taken from above in that drawing figure.

As indicated in FIG. 47, cartridge 115 also carries a staple pusher 461 and a staple biasing spring 463. Staple pusher, shown in detail in FIGS. 58-60, essentially takes the form of a flat plate 465 provided along two edges with a rim 467 and having an angled flange or wing 469 extending from another edge. Along an edge or long side of plate 465, rim 467 is formed with a rectangular recess 471, plate 465 having a rectangular finger 473 disposed next to the recess and in the plane of the plate. Finger 473 projects into an opening or window 474 (FIG. 53) provided on a rear wall of cartridge body portion 405 to limit the range of motion of staple pusher 461 within chamber 447 (FIG. 55).

Figure 61:
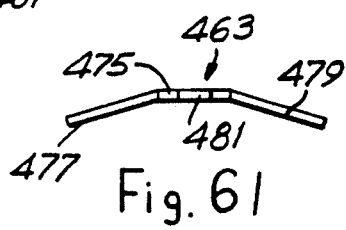
FIG. 61 is a side elevational view, on an enlarged scale, of a staple holding spring member shown in FIG. 47.
Figure 52:
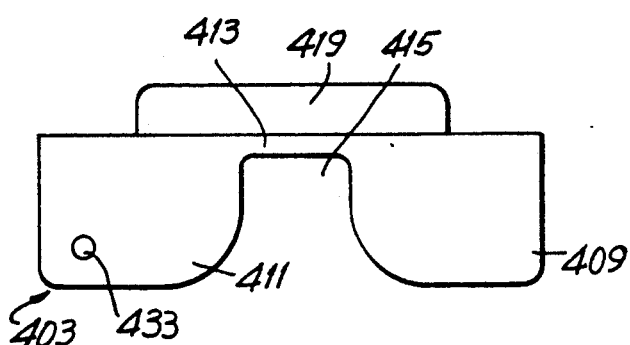
FIG. 52 is a bottom view of the cartridge body portion of FIGS. 49-51.
Figure 62:
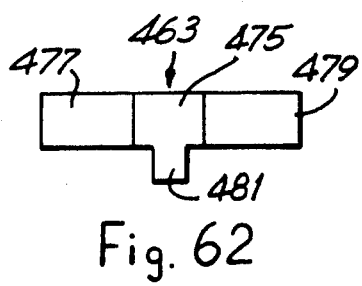
FIG. 62 is a top view of the staple holding spring of FIG. 61.

FIGS. 61 and 62 illustrate staple biasing spring 463 in detail. The spring includes a central body 475 having two wing-like extensions 477 and 479 projecting at an angle with respect to body 475. The body additionally has a neck or head projection 481 which, like finger 473 of staple pusher 461, passes through opening or window 474.

Staple and Staple Bending Operation

A staple 459, stainless steel or absorbable, used in a surgical instrument pursuant to the present invention comprises a pair of legs 483 and 485 connected to one another via a bight section 487, as shown in FIG. 63. Each leg 483 and 485 is oriented preferably at an acute angle $B_1$ of approximately 80° to 85° with respect to bight section 487. In addition, the free end of each leg 483 and 485 is chamfered at an angle $B_2$ of approximately 60° with respect to bight section 487. The inclination of the staple legs serves in part to prevent the legs from bending and to prevent the tissue from slipping off of the legs during a staple closing operation.

At the onset of a staple bending or deformation process, depicted in FIGS. 64-66, prongs 365 of staple forming and timing plate 117 engage bight section 487 at opposite ends thereof and push the bight section against anvil flange 197. As staple forming and timing plate 117 continues its forward or distal motion in response to a power stroke of actuator lever 120, bight section 487 bends inwardly at the edges of anvil 197 (FIG. 65). At the termination of the power stroke of actuator lever 120 and staple forming and timing plate 117, staple 459 has assumed a generally rectangular shape (FIG. 66) with the free ends of staple legs 483 and 485 overlapping one another in a criss-cross configuration. The inclination of the staple legs with respect to the bight portion and the concomitant criss-cross configuration of the staple legs in the bent state of the staple serves to tightly lock the tissue pieces to one another. It is to be noted that anvil flange 197 has a width which is less than the width of rectangular recess 367 so that prongs 365 can bend staple 459 around anvil flange 197 as shown in the drawing figures.

Cartridge Rotation Operation

Figure 71:
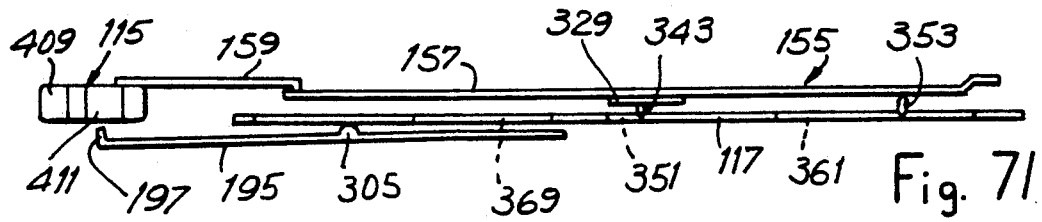
Figure 72:
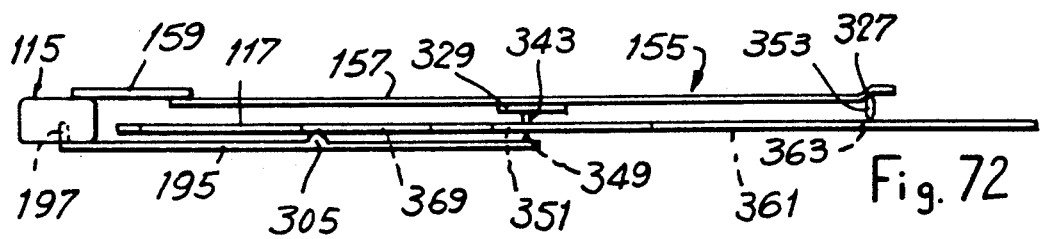
Figure 73:
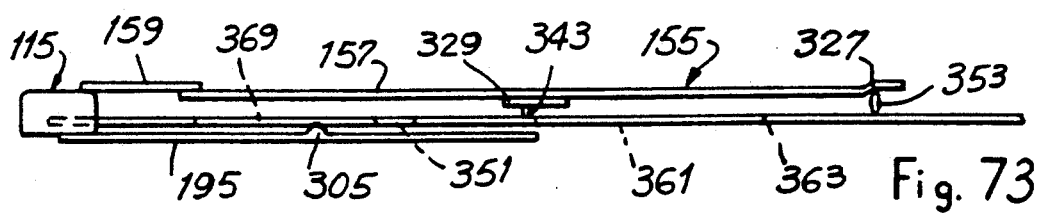
FIG. 73 is a diagram similar to FIGS. 67–72, showing the relative positions of the components of those drawing figures at the termination of the staple bending operation, shown in FIG. 66.

FIGS. 67 through 72 depict successive steps in the rotation of cartridge 115 by rotator assembly 155, while FIG. 73 shows a final stage in a staple bending operation. In a neutral or precocking configuration of the surgical instrument, shown in FIG. 67, anvil flange 197 rests against an outer surface of cartridge 115. In addition, staple release lever 169 is in an angled or opened orientation in which the leading segment 397 of the staple release lever is removed from the staple path along magazine slot 281 (FIGS. 20-21, 23-25 and 45). In this orientation of staple release lever 169, staples 459 can be shifted by staple pusher 175 and compression spring 177 (FIG. 3) from magazine slot 281 through staple entrance gap 453 (FIG. 56) into staple holding chamber 447 (FIG. 55) of cartridge 115. Provided that the staple holding chamber is not already filled with surgical staples 459, an additional staple entering the cartridge through gap 453 slides against flange or wing 469 of pusher 461 and into the cartridge.

In the neutral or precocking configuration of the instrument, U-shaped camming segment 399 of staple release lever 169 is partially disposed in recess 367 at the distal end of staple forming and timing plate 117 (alternatively, segment 399 may be disposed distally of a prong 365 of plate 117). Under pressure exerted by leaf spring 161 (FIG. 3), rotator pin 343 engages a major surface or face of staple forming and timing plate 117 proximally of slot 369, while floating pin 353 projects downwardly into slot 361 (see also FIG. 38).

Figure 68:
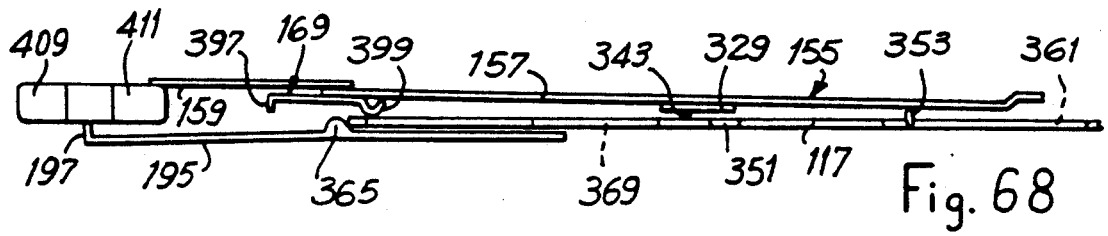

Upon the initiation of a cartridge rotation operation, staple release lever 169 is pivoted about hump 287 (FIGS. 20 and 24) by the engagement of U-shaped camming segment 399 with a leading end of staple forming and timing plate 117. As illustrated in FIG. 68, staple release lever 169 is rotated into a staple holding orientation generally parallel to staple forming and timing plate 117. In this orientation of the staple release lever, leading segment 397 thereof extends at least partially into magazine slot 281 and locks the staples therein against shifting towards cartridge 115 (see FIG. 45). Inasmuch as staple release lever 169 maintains the same staple holding orientation throughout the remainder of the cartridge rotation cycle, the staple release lever has been omitted from FIGS. 69-73.

Figure 69:
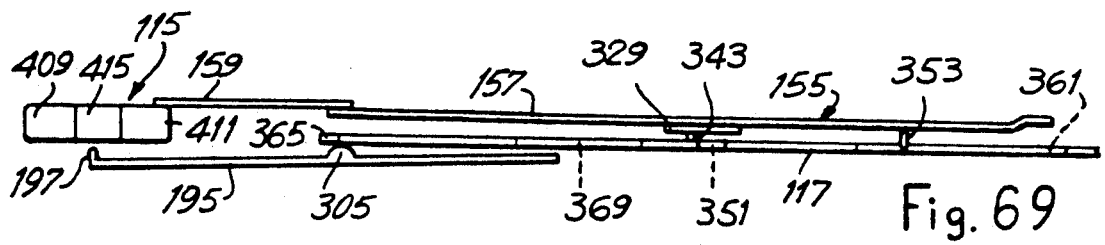

Upon further forward motion of staple forming and timing plate 117 during a cocking of the instrument via pushbutton 109 (FIGS. 1-3), camming projection 305 on anvil member 197 contacts a prong 365 of plate 117 and, in camming against that plate, further bends the anvil member and concomitantly shifts anvil flange 197 from cartridge 115, as indicated in FIG. 69.

Figure 70:
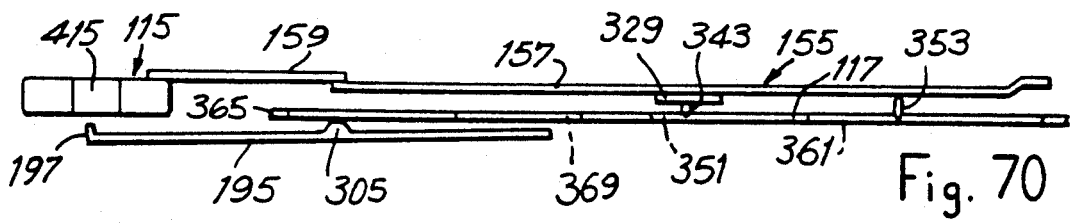

After the lateral shifting of anvil flange 197 and upon further forward motion of staple forming and timing plate 117, rotator pin 343 drops into slot 351 on staple forming and timing plate 117 under pressure exerted on the pin by leaf spring 161. The conical free end 345 of pin 343 then contacts the beveled proximal end 349 of slot 351 (FIG. 70). As stated above, the angles of inclination of conical end 345 and beveled end 349 and the associated coefficients of friction are such that rotator member 157 is entrained by staple forming and timing plate 117. Upon engagement of conical pin end 345 and beveled slot end 349, forward motion of the staple forming and timing plate pushes rotator member 157 and rotator link 159 towards the distal end of the instrument. That longitudinal motion causes a rotation of cartridge 115, as indicated in FIGS. 70-72.

Upon a 90° rotation of cartridge 115, the distal end of spacer element 329 abuts against shoulder 275 (FIG. 20) and thereby prevents further forward motion of rotator member 157. Further forward motion of staple forming and timing plate 117 during the cocking operation causes pin 343 to cammingly slide along beveled end 349 of slot 351 and thereby shift in a transverse direction in opposition to the biasing force exerted by leaf spring 161. Pin 343 then once again contacts a major longitudinal surface of the staple forming and timing plate (FIGS. 72 and 73). At the same time, floating pin 353 ascends beveled end 363 of slot 361 and engages inclined web 327 to lock rotator member 157 against rearward or proximal motion. Subsequently, camming projection 305 on anvil member 195 enters slot 369 in staple forming and timing plate 117. Upon the termination of a cocking operation executed via pushbutton 109 (FIG. 1-3), the various operative components of the surgical instrument have the prefiring configuration illustrated in FIG. 72.

During the power stroke of actuator lever 120 and staple forming and timing plate 117, camming projection 305 is disposed within slot 369 of the staple forming and timing plate, while the rotator assembly 155 remains locked into position by the coaction of spacer element 329 and shoulder 275, on the one hand, and floating pin 353 and inclined web 327, on the other hand. The power stroke of the device deforms a staple 459 into a closed configuration, as discussed hereinabove with reference to FIGS. 64-66.

Use in Corrective Surgery

Figure 74:
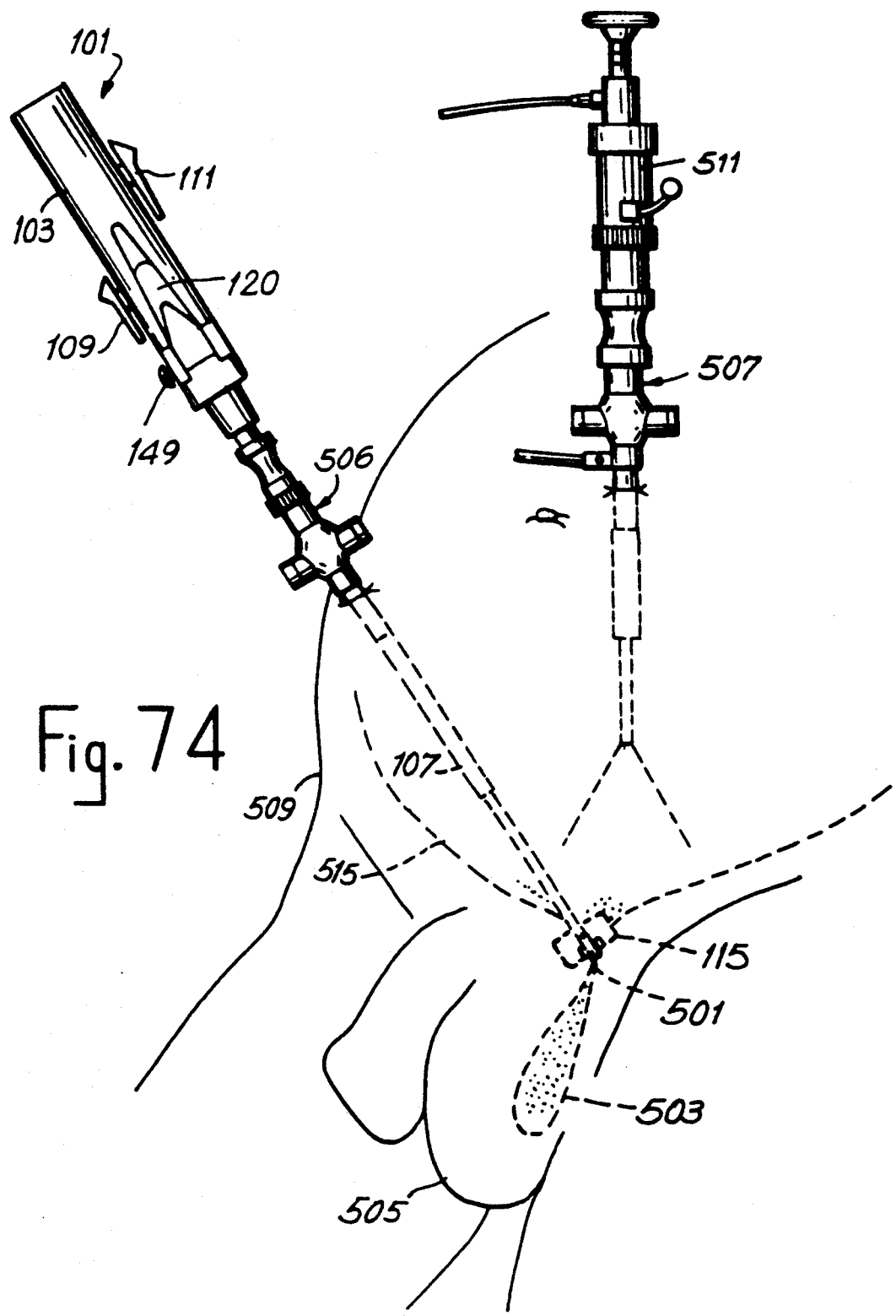
FIG. 74 is a schematic perspective view of a patient with a hernial tear in a region about the patient's scrotum, showing use of the instrument of FIG. 1 in a procedure carried out in accordance with the present invention.

FIG. 74 illustrates a stage in a surgical procedure using an instrument 101 in accordance with the present invention. As indicated in the drawing, a hernial opening 501 in the abdominal wall of a patient ay lead to a hernial sac 503 which may contain intestinal material. Both hernial sac 503 and the intestinal material contained therein may lie in the scrotal sac 505.

According to the invention, the neck of hernial sac 503 is closed intra-abdominally with the aid of conventional insufflation according to conventional laparoscopic abdominal procedures. The abdomen is insufflated conventionally using a conventional $CO_2$ insufflator and a conventional Veress needle. Two trocars and cannulas 506a, 507a each having a diameter of less than about ¼ with removable trocars 506b, 507b are inserted into the abdomen 509. Trocars and cannulas 506a,b and 507a,b, depicted in FIGS. 75 and 76, respectively, are conventional. Each cannula with trocar 506a,b, 507a,b is inserted into the abdomen conventionally and the respective trocar 506b, 507b removed. Each cannula 506a, 507a includes a trumpet valve that closes and seals the respective cannula after the respective trocar is removed to maintain insufflation. The cannulas with trocars 506a,b, 507a,b are inserted above the scarpia's fascia in the area surrounding the navel. With the trocar removed from the respective cannula, the valve of the cannula seals and maintains pressure inside the insufflated abdomen. An operating laparoscope 511 is inserted through cannula 507a and is used to locate the hernial orifice and view the entire procedure intra-abdominally. Surgical instrument 101 according to the invention is inserted into the insufflated abdomen through cannula 506a. Instrument 101 is long enough to reach the hernial defect from the point of the external opening (lateral to the navel). The surgical instrument has an inner pressure seal 150, 156 (FIGS. 3-3B) to keep gas from escaping from the insufflated abdomen and is shaped so as to seal when slid into cannula 506a. Cannula 507a includes a gas port 507c through which gas pressure in the insufflated abdomen is maintained via tubing and conventional equipment.

A distal portion of instrument 101, with the staple cartridge 115 aligned with the superstructure 107, is inserted through cannula 506 and advanced through the body cavity 515 so that a distal end of the instrument lies close to the hernial opening 501 while remaining on the internal side of the opening. As described hereinabove with reference to FIGS. 67-72, button 109 is then pushed in a distal direction to rotate cartridge 115 and to put the instrument 101 in a prefiring configuration. Subsequently, button 111 is pushed forwardly to open tong-like gripper members 121 and 123 and to shift them in the distal direction. The instrument is then manipulated until the inwardly turned hooks 231 and 233 pierce and have been inserted into respective parts of peritoneum tissue on opposite sides of, and at points near an end of, hernial opening 501. Button 111 is released and tension spring 143 (FIG. 3) pulls gripper members 121 and 123 rearwardly so that the two pieces of body tissue on opposite sides of the hernial opening 501 are pierced and gripped, approximated and held together by tissue positioning assembly 113. It is to be noted at this juncture that the tissue gripping, approximating and holding is accomplished from the internal side of the hernial opening which presents a concave surface to the instrument. Providing the instrument with hooks 231 and 233 enables the instrument to grip the concave peritoneum tissue, as described above.

Upon the retraction and closing of tong-like gripper members 121 and 123 through the action of tension spring 143, the two pieces of body tissue are stapled together from the internal side of the opening, the step of stapling being performed by squeezing actuator lever 120 against handle portion 103 of the instrument. The staple 459 is then bent into a closed configuration holding the two pieces of tissue together, as discussed hereinabove.

Upon the execution of the first stapling operation, tissue positioning assembly 113 is operated to release the gripped tissues and cartridge 115 is rotated back into a longitudinal orientation in which the cartridge is aligned with superstructure assembly 107. This counter-rotation enables the loading of another staple into cartridge 115 and the removal of the formed staple suture from the anvil flange 197. Cartridge 115 is then rotated again as described hereinabove with respect to FIGS. 67-72, whereupon the instrument is again manipulated to insert hooks 231 and 233 into the respective pieces of internal body tissue on opposite sides of hernial tear 501 at points proximate to but spaced from the suture. As before, button 111 is released and tension spring 143 (FIG. 3) pulls gripper members 121 and 123 rearwardly so that the two pieces of body tissue on opposite sides of the hernial opening 501 are gripped, approximated and held together by tissue positioning assembly 113. The operation proceeds in this manner until the hernial opening or tear 501 is closed. Subsequently, the staple cartridge is rotated into its longitudinal or aligned orientation prior to removal of instrument 101 from the patient's body 509.

Although the invention has been described in terms of particular embodiments and applications, one of ordinary skill in the art, in light of this teaching, can generate additional embodiments and modifications without departing from the spirit of or exceeding the scope of the claimed invention. For example, the invention is applicable to joining body tissue in general, and to joining body tissue in body cavities in particular. Devices other than surgical staples may be used to accomplish the tissue joining, as for example the staple-like clip disclosed in application Ser. No. 07/195,586. Accordingly, it is to be understood that the drawings and descriptions herein are proffered by way of example to facilitate comprehension of the invention and should not be construed to limit the scope thereof.

What is claimed is:

1. A procedure for joining body tissue in a body cavity from within the body cavity through a small opening into the body cavity which is remove from the body tissue to be joined, comprising:

insufflating a body cavity;

inserting a cannula into said cavity through an opening into said cavity remote from the body tissue to be joined, said cannula providing a selectively sealable opening into said cavity through which a tissue-joining instrument may be introduced into said cavity with a fluid-tight seal between said cannula and said instrument inserted therethrough and with a fluid-tight seal between said cannula and tissue defining said opening through which said cannula is inserted, said seals being effective to substantially maintain insufflation of said cavity when said cannula is inserted in said body opening and said instrument is inserted into said cavity;

providing an instrument having a distal end which includes means for applying a clip-like or staple-like device for piercing and joining body tissue, a proximal end from which said means for applying at said distal end, is activated to apply said clip-like or staple-like device, and a fluid-tight internal seal between said distal and proximal ends effective to substantially maintain insufflation of said cavity when said instrument is in said cannula;

inserting said instrument into said insufflated cavity through said cannula and positioning said distal end of said instrument remote from said opening near said body tissue to be joined; and activating said means for applying said clip-like or staple-like device to join said body tissue with a said clip-like or staple-like device applied by said instrument distal end in said insufflated cavity.

2. The procedure according to claim 1 including the step of introducing a laparoscope into said cavity.

3. A procedure for intra-abdominally repairing a hernia, comprising:

insufflating the abdomen of a patient;

inserting a cannula into said abdomen to provide a selectively sealable opening into said abdomen through which a stapling instrument may be introduced into said abdomen, said cannula providing a fluid-tight seal between said cannula and said stapling instrument and a fluid-tight seal between said cannula and tissue defining an opening through which said cannula is inserted, said seals being effective to substantially maintain insufflation of said abdomen;

providing a stapling instrument which applies a clip-like or staple-like device for piercing and joining body tissue and which has a fluid-tight internal seal effective to substantially maintain insufflation of said abdomen;

inserting said instrument into said abdomen through said cannula; and stapling said body tissue with said stapling instrument adjacent a hernia to repair it.

4. The procedure according to claim 3 including the step of introducing a laparoscope into said abdomen.

5. The procedure according to claim 3 wherein said cannula is inserted above the scarpia's fascia of said patient.

6. A method for stapling body tissue of a patient situated in an internal body cavity of the patient from within the body cavity through a small opening into the body cavity, said method comprising the steps of:

making a small opening into the body cavity at a site on the patient's body remote from body tissue to be stapled in an internal body cavity;

insufflating said body cavity;

inserting an elongate stapling instrument through said small opening;

moving said instrument through said small opening and through said insufflated internal body cavity so that a distal end of said instrument is close to said body tissue to be stapled and on an internal side of said body tissue in said body cavity;

gripping, approximating and holding together in a stapling position two pieces of said body tissue from said internal side thereof, the composite step of gripping, approximating and holding being performed remotely from the body tissue pieces with said instrument by manipulation at a proximal end thereof; and stapling together said two pieces of said body tissue from said internal side, said step of stapling being performed with said instrument by manipulation at said proximal end thereof.

7. The method defined in claim 6, further comprising the step of rotating a staple-storing cartridge at said distal end of said instrument upon insertion thereof through said small opening into said body cavity, said step of rotating being accomplished via manipulation at said proximal end of said instrument.

8. The method defined in claim 7 wherein said composite step of gripping, approximating and holding includes the steps of inserting ends of tong-like gripper members into said two pieces of body tissue and moving said tong-like gripper members towards one another and towards said distal end of said instrument.

9. The method defined in claim 8 wherein said composite step of gripping, approximating and holding is accomplished by manipulation of a first mechanism of said instrument, including said tong-like gripper members, and wherein said step of stapling is accomplished by manipulation of a second mechanism of said instrument separate and distinct from said first mechanism.

10. The method defined in claim 6, further comprising the step of inserting a distal end of a laparoscope into said body cavity to provide for visual inspection of said body tissue and the distal end of said instrument during a stapling operation.

11. The method defined in claim 10 wherein said distal end of said laparoscope is inserted through another small opening of the patient different from said small opening.

12. The method defined in claim 6 wherein said small opening is up to approximately one-half inch wide.

13. The method defined in claim 6 wherein said composite step of gripping, approximating and holding includes the steps of inserting ends of tong-like gripper members into said two pieces of body tissue and moving said tong-like gripper members towards one another and towards said distal end of said instrument.

14. The method defined in claim 13 wherein said composite step of gripping, approximating and holding is accomplished by manipulation of a first mechanism of said instrument, including said tong-like gripper members, and wherein said step of stapling is accomplished by manipulation of a second mechanism of said instrument separate and distinct from said first mechanism.

15. A method for stapling body tissue of a patient to close an internal opening in a body wall situated in an internal body cavity of the patient from within the body cavity through a small opening into the body cavity, said method comprising the steps of:

making a small opening into an internal body cavity at a site on a patient's body remote from body tissue to be stapled;

insufflating said internal body cavity;

inserting an elongate stapling instrument through said small opening;

moving said instrument through said small opening and through said insufflated internal body cavity so that a distal end of said instrument is close to and on an internal side of an internal opening in said body cavity;

gripping, approximating and holding together in a stapling position two pieces of said body tissue on opposite sides of said internal opening from said internal side thereof, the composite step of gripping, approximating and holding being performed remotely from said internal opening with said instrument by manipulation at a proximal end thereof; and stapling together said two pieces of said body tissue to close said internal opening from said internal side, said step of stapling being performed with said instrument by manipulation at said proximal end thereof.

16. The method defined in claim 15, further comprising the step of rotating a staple-storing cartridge at said distal end of said instrument upon insertion thereof through said small opening into said body cavity, said step of rotating being accomplished via manipulation at said proximal end of said instrument.

17. The method defined in claim 16 wherein said composite step of gripping, approximating and holding includes the steps of inserting ends of tong-like gripper members into said two pieces of body tissue and moving said tong-like gripper members towards one another and towards said distal end of said instrument.

18. The method defined in claim 17 wherein said composite step of gripping, approximating and holding is accomplished by manipulation of a first mechanism of said instrument, including said tong-like gripper members, and wherein said step of stapling is accomplished by manipulation of a second mechanism of said instrument separate and distinct from said first mechanism.

19. The method defined in claim 16, further comprising the step of inserting a distal end of a laparoscope into said body cavity to provide for visual inspection of said body tissue and the distal end of said instrument during a stapling operation.

20. The method defined in claim 19 wherein said distal end of said laparoscope is inserted through another small opening of the patient different from said small opening.

21. The method defined in claim 15 wherein said small opening is up to approximately one-half inch wide.

22. The method defined in claim 15 wherein said composite step of gripping, approximating and holding includes the steps of inserting ends of tong-like gripper members into said two pieces of body tissue and moving said tong-like gripper members towards one another and towards said distal end of said instrument.

23. The method defined in claim 15 wherein said composite step of gripping, approximating and holding is accomplished by manipulation of a first mechanism of said instrument, including said tong-like gripper members, and wherein said step of stapling is accomplished by manipulation of a second mechanism of said instrument separate and distinct from said first mechanism.

* * * * *

UNITED STATES PATENT AND TRADEMARK OFFICE
CERTIFICATE OF CORRECTION

PATENT NO. : 5,220,928
DATED : June 22, 1993
INVENTOR(S) : Robert Oddsen et al

It is certified that error appears in the above-indentified patent and that said Letters Patent is hereby corrected as shown below:

Column 23 line 66, change "remove" to --remote--.

Signed and Sealed this

Twenty-seventh Day of December, 1994

Attest:

BRUCE LEHMAN

Attesting Officer     Commissioner of Patents and Trademarks